United States Patent [19]
Green et al.

[11] Patent Number: 6,100,380
[45] Date of Patent: Aug. 8, 2000

[54] IMMUNOMODULATING PEPTIDES AND METHODS OF USE

[75] Inventors: Lawrence R. Green, Tacoma, Wash.;
Nickolai V. Sinakevich, St. Petersburg, Russian Federation; Vadim T. Ivanov, Moscow, Russian Federation; Inessa I. Mikhalyova, Moscow, Russian Federation; Boris V. Vaskovsky, Moscow, Russian Federation; Alexander N. Mikhaltsov, St. Petersburg, Russian Federation; Vyacheslav G. Morozov, St. Petersburg, Russian Federation; Vladimir K. Khavinson, St. Petersburg, Russian Federation

[73] Assignee: Cytran, Inc., Kirkland, Wash.

[21] Appl. No.: 08/484,511

[22] Filed: Jun. 7, 1995

Related U.S. Application Data

[63] Continuation-in-part of application No. 08/144,779, Oct. 28, 1993, and application No. 07/816,205, Jan. 2, 1992, abandoned, said application No. 08/144,779, Oct. 28, 1993, is a continuation-in-part of application No. 07/967,633, Oct. 28, 1992, abandoned, which is a continuation-in-part of application No. 07/783,517, Oct. 28, 1991, abandoned.

[51] Int. Cl.[7] .............................. A61K 38/00; C07K 5/00; C07K 7/00

[52] U.S. Cl. ...................... 530/328; 530/329; 530/330; 530/300

[58] Field of Search ................................ 514/13, 14, 15, 514/16, 17, 181; 530/300, 324, 325, 326, 327, 328, 329, 330

[56] References Cited

U.S. PATENT DOCUMENTS

| | | |
|---|---|---|
| 3,803,118 | 4/1974 | Bennett et al. . |
| 4,002,602 | 1/1977 | Goldstein . |
| 4,010,148 | 3/1977 | Goldstein . |
| 4,038,282 | 7/1977 | Hirschmann et al. ................ 260/295 |
| 4,077,949 | 3/1978 | Goldstein . |
| 4,079,127 | 3/1978 | Goldstein et al. . |
| 4,116,951 | 9/1978 | Wang . |
| 4,120,951 | 10/1978 | Goldstein . |
| 4,133,804 | 1/1979 | Bach et al. . |
| 4,148,788 | 4/1979 | Wang . |
| 4,167,557 | 9/1979 | Goldstein . |
| 4,261,886 | 4/1981 | Goldstein et al. . |
| 4,264,571 | 4/1981 | Goldstein et al. . |
| 4,297,276 | 10/1981 | Goldstein et al. . |
| 4,339,427 | 7/1982 | Goldstein et al. . |
| 4,353,821 | 10/1982 | Birr et al. . |
| 4,374,828 | 2/1983 | Folkers et al. . |
| 4,377,511 | 3/1983 | Lopukhin et al. . |
| 4,388,234 | 6/1983 | Horecker . |
| 4,389,343 | 6/1983 | Horecker . |
| 4,395,404 | 7/1983 | Low et al. . |
| 4,396,605 | 8/1983 | Birr . |
| 4,426,324 | 1/1984 | Meienhofer . |
| 4,427,783 | 1/1984 | Newman et al. . |
| 4,428,938 | 1/1984 | Kisfaludy et al. . |
| 4,442,031 | 4/1984 | Felix et al. . |
| 4,466,918 | 8/1984 | Birr et al. . |
| 4,470,926 | 9/1984 | Birr et al. . |
| 4,500,450 | 2/1985 | Seipke et al. . |
| 4,505,853 | 3/1985 | Goldstein et al. . |
| 4,517,119 | 5/1985 | Felix et al. . |
| 4,526,717 | 7/1985 | Seipke et al. . |
| 4,571,336 | 2/1986 | Houck et al. . |
| 4,599,231 | 7/1986 | Milich et al. . |
| 4,612,365 | 9/1986 | Birr et al. . |
| 4,614,731 | 9/1986 | Horecker . |
| 4,621,135 | 11/1986 | Trainin et al. . |
| 4,634,682 | 1/1987 | Erickson et al. . |
| 4,659,694 | 4/1987 | Horecker . |
| 4,696,915 | 9/1987 | Horecker . |
| 4,699,898 | 10/1987 | Gottlieb . |
| 4,711,952 | 12/1987 | Kasafirek et al. . |
| 4,722,999 | 2/1988 | Handschumacher et al. . |
| 4,751,216 | 6/1988 | Gottlieb . |
| 4,814,434 | 3/1989 | Goldfarb . |
| 4,826,680 | 5/1989 | Jaeger . |
| 4,904,643 | 2/1990 | Brunetti et al. . |
| 4,910,296 | 3/1990 | Birr et al. . |
| 4,983,387 | 1/1991 | Goldstein et al. . |

FOREIGN PATENT DOCUMENTS

| | | |
|---|---|---|
| 0 164 654 | 5/1985 | European Pat. Off. . |
| 2583982 | 1/1987 | France . |
| 3421789 | 10/1988 | Germany . |
| 659586 | 2/1987 | Switzerland . |
| 1 363 801 | 8/1974 | United Kingdom . |
| 88/00255 | 7/1989 | WIPO . |

OTHER PUBLICATIONS

U.S. application No. 07/415,283, Yakovlev et al., filed Dec. 14, 1988.

Anisimov et al. (1982) *Mechanisms of Ageing and Development*, 19:245–258.

Anisimov et al. (1989) *Mechanisms of Ageing and Development*, 49:245–257.

Belokrylov et al. (1978) *Bulletin of Experimental Biology*, No. 7, 84:56–58.

Belokrylov et al. (1977) *Bulletin of Experimental Biology*, No. 7, 86:51–53.

Bespaluv et al. (1989) *Eksp. Onkol.*, Chemical Abstracts III, Abstract No. 146389R, 11(4) 23–6 (Russ).

*Cytomedins* (Bulletin), Apr. 13, 1990, Russia.

Gavrilenko et al. (1982) *Bulletin of Experimental Biology*, No. 4, 93:39–40.

Goldstein et al. (1972) *Proc. Natl. Acad. Sci. USA*, 69:1800–1803.

(List continued on next page.)

Primary Examiner—Avis M. Davenport
Attorney, Agent, or Firm—Townsend and Townsend and Crew

[57] ABSTRACT

This invention provides peptides of the formula R'-Glx-Glx-Lys-R" in which Glx is Glu or Gln. In particular, this invention provides the peptides Thr-Ala-Glu-Glu-Lys and Thr-Pro-Glu-Glu-Lys. This invention also provides pharmaceutical compositions comprising these peptides. The peptides of this invention are useful for immunomodulation.

39 Claims, 10 Drawing Sheets

OTHER PUBLICATIONS

R. S. Chen (1989) *Chemical Abstracts,* vol. 111(7), Abstract No. 55230R.

Fauszt et al. (1975) *Chemical Abstracts,* vol. 82(11), Abstract No. 73453C.

Khmelnitskii et al. (1983), *Bulletin of Experimental Biology,* No. 6, 95:123–124.

Kuznik et al. (1982), *Bulletin of Experimental Biology,* No. 9, 94;27–29.

Kusnik et al. (1981) *Bulletin of Experimental Biology,* No. 9, 92:264–266.

Low et al. (1981) *Proceedings of the National Academy of Science,* 78:1162–1166.

Rodionov, et al. (1990) "The Immunocorrective Therapy of Pyoderma Caused by Staphylococci Multiply Resistant to Antibiotics"; *Vestn. Dermatol. Venerol,* 1:42–45 (Medline Abstract No. 90224329).

Solovev et al. (1977) *Bulletin of Experimental Biology,* No. 9, 84:355–358.

Solovev et al. (1983) *Bulletin of Experimental Biology,* No. 6, 95:123–124.

"Thymogen" (Bulletin), Nov. 11, 1989, published by Cytomed (Leningrad).

Yakovlev et al., (1990) *Resistance Stress Regulation,* Nauka Publishers (Leningrad), pp. 90–93, 174–205.

Two brochures in Russian (no English translation).

*Remington's Pharmaceutical Science,* 17th ed., Mack Publishing Co., Easton, PA (1985).

Stewart and Young, *Solid Phase Peptide Synthesis,* 2nd ed., Pierce Chemical Company (1984).

Maniatis et al., (1982) *Molecular Cloning, A Laboratory Manual,* Cold Spring Harbor Laboratory.

Tam et al. (1983) *J. Am. Chem. Soc.,* 105:6442.

Declaration of Lawrence R. Green.

R.S. Chen; "Monte Carlo Simulations for the Study of Hemoglobin–Fragment Conformations"; Journal of Computational Chemistry, vol. 10, No. 4, pp. 488–494 (1989).

CA 78:43980, 1973, Bennett et al.

R.S. Chen, CA 111:55230r, 1989.

Hirschmann et al., CA 79:66820e, 1973.

Giori et al., CA 89:215752v, 1978.

Cola et al., CA 111: 129603p, 1989.

Peptide EK Influence on Percent Suvival for Mice Administered 10 x LD50 S. aureus with and without Amplcillin Co-administration

*Peptide EK Influence on Percent Suvival for Mice Administered 10 x LD50 S. aureus without Ampicillin*

*Peptide EK Influence on Percent Suvival for Mice Administered 10 x LD50 S. aureus with the Co-administration of Ampicillin MED*

Fig. 5

Microorganism $LD_{50}$ Determination in Mice:

Infecting Microorganism (S. aureus, MR)　　　10 g Mucin/100 ml saline
⇓　　　　　　　　　　　　　　　　　　　　　　　　　　　　　　⇓

Brain-heart infusion broth concentrated　　　　Adjust to pH 6.8
1.5 fold (Shake at 30° C, 2 hours)　　　　　　(with 1% NaOH)
⇓　　　　　　　　　　　　　　　　　　　　　　　　　　　　　　⇓

Centrifuge 3000 rpm, 20 min　　　　　　　　　Sterilization 120° C,
　　　　　　　　　　　　　　　　　　　　　　　　　　　　　30 min
⇓　　　　　　　　　　　　　　　　　　　　　　　　　　　　　　⇓
⇓　　　　　　　　　　　　　　　　　　　　　　　　　　　　　　⇓
Discard _____　　　　　　　⇓
Supernatant　　　Resuspend in BHI　　　　　　10 % mucin solution
　　　　　　　　　　⇓_____⇓
　　　　　　　　　　　　　　　　　⇓
　　　　　　　　　　　　　　　　　⇓

$LD_{50}$ Determination
10 x LD50 dose inoculum for Ampicillin i.p.
administered to each test group

⇓

Test Substance Evaluation

Inoculum Dose 10 x LD50 i.p. in mice

⇓ i.p. Administer Ampicillin (animals
pretreated with HM897 dose 1000, 100, 10 μg/kg)

⇓
⇓

Survival Percent 72 hours

*Peptide HM897 Influence on Percent Survival for Mice Administered 10 x LD50 S. aureus without Ampicillin*

*Peptide HM897 Influence on Percent Survival for Mice Administered 10 x LD50 S. aureus with the Co-administration of Ampicillin MED*

*HM897 Influence on Percent Survivors for Vacinated Rainbow Trout Infected with Vibrio anguillarum*

* 50 t. out inoculated with Vibrio anguillarum 7 days after a 5 minute expo: ure toTest Article in a 38 liter tank per study group

```
                         SEQUENCE LISTING (1) GENERAL INFORMATION:

(iii) NUMBER OF SEQUENCES: 8

(2) INFORMATION FOR SEQ ID NO:1:

(i) SEQUENCE CHARACTERISTICS:
          (A) LENGTH: 5 amino acids
          (B) TYPE: amino acid
          (C) STRANDEDNESS: single
          (D) TOPOLOGY: linear (ii) MOLECULE TYPE: peptide (xi) SEQUENCE DESCRIPTION: SEQ ID NO:1:

Thr Pro Glu Glu Lys
1               5

(2) INFORMATION FOR SEQ ID NO:2:

(i) SEQUENCE CHARACTERISTICS:
          (A) LENGTH: 5 amino acids
          (B) TYPE: amino acid
          (C) STRANDEDNESS: single
          (D) TOPOLOGY: linear (ii) MOLECULE TYPE: peptide (xi) SEQUENCE DESCRIPTION: SEQ ID NO:2:

Thr Ala Glu Glu Lys
1               5

(2) INFORMATION FOR SEQ ID NO:3:

(i) SEQUENCE CHARACTERISTICS:
          (A) LENGTH: 7 amino acids
          (B) TYPE: amino acid
          (C) STRANDEDNESS: single
          (D) TOPOLOGY: linear (ii) MOLECULE TYPE: peptide (xi) SEQUENCE DESCRIPTION: SEQ ID NO:3:

Glu Lys Thr Ala Glu Glu Lys
1               5

(2) INFORMATION FOR SEQ ID NO:4:

(i) SEQUENCE CHARACTERISTICS:
          (A) LENGTH: 5 amino acids
          (B) TYPE: amino acid
          (C) STRANDEDNESS: single
          (D) TOPOLOGY: linear (ii) MOLECULE TYPE: peptide (xi) SEQUENCE DESCRIPTION: SEQ ID NO:4:
```

```
Met Leu Thr Ala Glx
1               5
```

(2) INFORMATION FOR SEQ ID NO:5:

(i) SEQUENCE CHARACTERISTICS:
        (A) LENGTH: 4 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:5:

```
Leu Thr Ala Glx
1
```

(2) INFORMATION FOR SEQ ID NO:6:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:6:

```
Thr Ala Glx Glx Lys
1               5
```

(2) INFORMATION FOR SEQ ID NO:7:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:7:

```
Thr Ala Gln Glu Lys
1               5
```

(2) INFORMATION FOR SEQ ID NO:8:

(i) SEQUENCE CHARACTERISTICS:
        (A) LENGTH: 4 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:8:

```
Thr Glu Gln Lys
```

IMMUNOMODULATING PEPTIDES AND METHODS OF USE

This application is a continuation-in-part of Ser. No. 08/144,779, ('779) filed Oct. 28, 1993 and Ser. No. 07/816,205 ('205), filed Jan. 2, 1992 (now abandoned). Ser. No. '779 is a continuation-in-part of Ser. No. 07/967,633 ('633), filed Oct. 28, 1992 (now abandoned) which is a continuation-in-part application of Ser. No. 07/783,517 ('517), filed Oct. 28, 1991 (now abandoned). The disclosures in Ser. Nos. '779, '205, '633, and '517 are incorporated herein by reference.

The present invention relates to peptide pharmaceutical preparations and uses thereof, in particular, peptides including the amino acid sequence, Glx-Lys. The pharmaceutical preparations find uses in (i) modulating the immune system e.g. in immunodepressed and immunocompromised subjects at an increased relative risk of developing an opportunistic infection; (ii) augmentating immune responses to vaccines; (iii) treating atopic type I hypersensitivity states e.g. allergy; and (iv), treating anemia.

BACKGROUND OF THE INVENTION

Immune depression is a common clinical sequelae in certain chronic and acute bacterial, viral and parasitic infections. In other diseases toxemia may reduce bone marrow capacity with resultant anemia and abnormalities of the immune system. The immune system is responsible for host resistance to diseases, and immunodepression or immunosuppression can predispose infection with one or more infectious agents, commonly known as opportunistic infections. A loss of immune system activity often results in serious and life-threatening diseases. Such functional abnormalities may be present in any of the cellular or humoral components of the immune system, e.g., granulocytes, lymphocytes, complement, antibody, etc. Animals having dysfunctional immune systems may also be at an increased risk of malignancy.

Inmunodeficiencies may result from many etiologies including a primary hereditary genetic abnormality (e.g., Chediak-Higashi Syndrome, Severe Combined Immunodeficiency, Chronic Granulomatous Disease, DiGeorge Syndrome); or, may be acquired as a result of accidental exposure, e.g., to radiation, heavy metals, insecticides, or, from therapeutic intervention e.g., chemotherapy with glucocorticoids or radiation therapy, or acquired as a results of infection e.g., with HIV, CMV, Mycobacteria, or a parasite. Patients with a primary or an acquired immunodeficiency would benefit from methods for stimulating the immune system.

Diseases may also result from loss of regulatory control within the immune system. For example autoimmune diseases such as multiple sclerosis, rheumatoid arthritis, systemic lupus erythematosus, Sjogren's syndrome, and type II diabetes may result from improper recognition of "self" tissues as "foreign". Treatments may include generalized non-specific immune suppression that can result in an increase in the incidence of infections and malignancy. Methods to compensate for decreased anti-microbial resistance during chemotherapy (or radiation therapy) are of great medical importance.

Immunological stimulation, even in healthy individuals, may aid in the treatment or prevention of disease. For example, stimulating an immune response to a vaccine, referred to herein as vaccine augmentation, could improve the duration or strength of protection afforded by the procedure. Also, specific immunization with tumor antigens has been shown in certain circumstances to result in tumor remission. Drugs used in treatment of cancer and infection have significant side effects, and use of an immunostimulatory agent could make it possible to reduce the dose of the a drug to a less toxic level.

Thus, there is a need in the art for compositions and methods that modulate, i.e., stimulate or depresses, the immune system. Ideally, a candidate compound or method would be (i) capable of stimulating or suppressing immunity, dependent upon the immune status of the patient at the time of treatment; and, (ii) be able to restore a natural balance to a dysfunctional immune system. Quite surprisingly, the present invention fulfills these and other related needs.

SUMMARY OF THE INVENTION

The present invention provides compositions comprising a peptide having the formula R'-Glx-Glx-Lys-R" or a pharmaceutically acceptable salt thereof; wherein Glx is Glu or Gln; R' is H- or a first amino acid sequence having fewer than 7 amino acids; R" is -H or a second amino acid sequence having fewer than 7 amino acids; and the peptide has a sequence of at least 5 and not more than 9 amino acids.

Generally, R' is H-, Thr-Ala-, Thr-Pro-, Ser-Ala-, Ser-Pro-, Ser-Ser-, Met-Leu-Thr-Ala- [SEQ ID NO:3], or Leu-Thr-Ala-; and R" is -H. -Ala, -Ala-Ala or -Ala-Val. In preferred embodiments, the peptide is L-Thr-L-Pro-L-Glu-L-Glu-L-Lys [SEQ ID NO:1] or L-Thr-L-Ala-L-Glu-L-Glu-L-Lys [SEQ ID NO:2].

Also provided are pharmaceutical preparations comprising a peptide having the formula R'-Glx-Lys-R" or a pharmaceutically acceptable salt thereof, wherein Glx is Glu or Gln; R' is H- or a first amino acid sequence having fewer than 7 amino acids; R" is -H or a second amino acid sequence having fewer than 7 amino acids; and the peptide has a sequence of at least 2 and not more than 9 amino acids; and a physiologically acceptable carrier. In preferred embodiments, the peptide is L-Glu-L-Lys, L-Thr-L-Ala-L-Glu-L-Glu-L-Lys [SEQ ID NO:2] or L-Thr-L-Pro-L-Glu-L-Glu-L-Lys [SEQ ID NO:1].

Methods for using the peptides of the present invention are also provided. These methods include administration of the pharmaceutical preparations of the present invention for immunomodulation of a host's immune system, treatment of infections, treatment of anemias, treatment of atopic states, and treatment of immune disorders.

BRIEF DESCRIPTION OF THE FIGURES

FIG. 5 illustrates an experimental protocol to assess the efficacy of HM897 in the treatment of bacterial infection in mice.

DESCRIPTION OF THE PREFERRED EMBODIMENT

Figure 1:
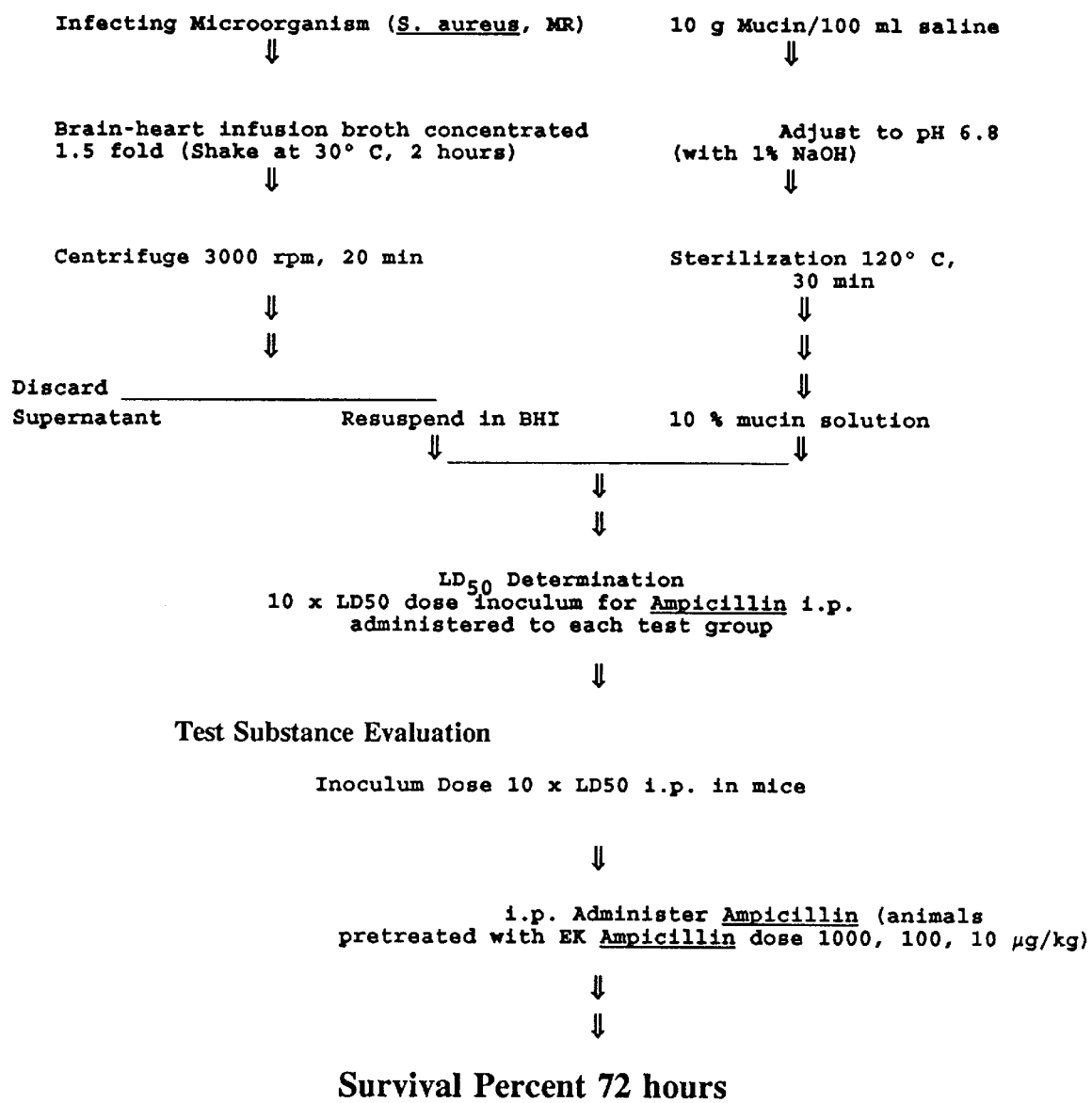
FIG. 1 illustrates an experimental method for assessing treatment of infection with EK.

The present invention is based in part on the discovery that certain peptide compositions exhibit a broad range of efficacy for modulation of the immune system. This provides a means for the prevention and treatment of infections in immunocompetent as well as immunodepressed states, and for therapeutically effective treatment of immunodeficient states, particularly AIDS. Other disorders associated with immune and hematologic systems may be similarly treated. This is believed to be highly unexpected for such relatively small compounds to exhibit such a broad range of activity. Furthermore, we have not found any significant side effects from the use of the peptides according to the present invention. Due to their simple nature, the peptides of the present invention are relatively inexpensive to manufacture.

The present invention provides peptide compositions, pharmaceutical preparations containing the peptides, and methods for therapeutic use of the peptides. Generally, the compositions comprise a peptide having the formula R'-Glx-Glx-Lys-R" or a pharmaceutically acceptable salt thereof; wherein Glx is Glu or Gln; R' is H- or a first amino acid sequence having fewer than 7 amino acids; R" is -H or a second amino acid sequence having fewer than 7 amino acids; and the peptide has a sequence of at least 5 and not more than 9 amino acids.

The pharmaceutical preparations of the present invention generally comprise a peptide having the formula R'-Glx-Lys-R" or a pharmaceutically acceptable salt thereof, wherein Glx is Glu or Gln; R' is H- or a first amino acid sequence having fewer than 7 amino acids; R" is -H or a second amino acid sequence having fewer than 7 amino acids; and the peptide has a sequence of at least 2 and not more than 9 amino acids; and a physiologically acceptable carrier. The subject peptides and pharmaceutical preparations may be employed in a variety of therapeutic uses. Uses include modulating the activity of a subject's immune system, treating infections in a host, treating atopic states, treating immune disorders, treating anemias in a host, and augmenting vaccination responses.

As used herein, the terms "immunomodulator" and "immunomodulating" mean the agent for, and an activity of, restoring a natural balance in a host's immune system. This includes stimulating and increase in, or decrease in a cellular or humoral activity of the subject's immune system, as evidenced by measurable blood parameters and/or the patient's improved ability to combat infection or disease, and/or the ability to heal tissue, and/or an in vitro measurement of a cellular or humoral activity of the subject. Immunomodulation means stimulating an increase in a host's immune system from an immunodeficient state (for example, caused by a genetic abnormality or removal of the thymus), and/or an immunodepressed state (for example, caused by exposure to radiation or chemotherapeutic drugs) to a more normal state (e.g., comparable to that in a normal healthy subject). Moreover, in alternative embodiments the instant invention provides for modulation/decreasing the activity of an immune system, (e.g., in a patient having an autoimmune disease) by lowering blood parameters and other indicia of the immune state if these indicia are abnormally elevated (e.g., rheumatoid factor in rheumatoid arthritis).

Embodiments of the invention include therapeutic methods for treating subjects having an immunodeficient, immunodepressed, elevated and/or autoimmune state thereby to provide prophylactic or thereapeutic treatments of infection and wound healing.

Generally, the peptide will have a structure according to Formula I, wherein according to convention the first named amino acid is the amino terminus and the last named amino acid is the carboxyl terminus.

R'-Glx-Lys-R"     (I)

wherein:

R' is H-, Thr-Ala-Glx-, Thr-Pro-Glx-, Ser-Ala-Glx-, Ser-Pro-Glx-, Ser-Ser-Glx-, Met-Leu-Thr-Ala-Glx- [SEQ ID NO:4], or Leu-Thr-Ala-Glx- [SEQ ID NO:5];

R" is -H, -Ala, -Ala-Ala or -Ala-Val; and Glx is Glu or Gln.

In accordance with a preferred embodiment of the present invention are pharmaceutical preparations comprising peptides according to Formula II;

R'-Glx-Glx-Lys-H     (II)

wherein:

R' is Thr-Ala-Glx-, Thr-Pro-Glx-, Ser-Ala-Glx-; Ser-Pro-Glx-, or Ser-Ser-Glx-.

Preferred species are Glx-Lys and Thr-Ala-Glx-Glx-Lys [SEQ ID NO:6], particularly wherein Glx=Glu.

The amino acids constituting the subject peptides of Formula I or II may be either a D- or an L-stereoisomer, and it anticipated that mixtures of D- and L-amino acids may be used within a subject peptide. It is presently preferred that all of the amino acids be natural amino acid of the L-form. Specific amino acid stereoisomers are denoted herein by a prefix of L- or D-.

For example, the L-stereoisomer of alanine is denoted L-Ala. Species in which R"=H indicates a free C-terminal carboxylic acid group.

Other particularly preferred species useful in accordance with the invention are the peptides according to Formula I wherein:

R'=Glx-

R'=Thr-Pro-Glx-

R'=Met-Leu-Thr-Ala-Glx- [SEQ ID NO:4] and R"=-Ala;

R'=Leu-Thr-Ala-Glx- [SEQ ID NO:5] and R"=-Ala;

R'=Leu-Thr-Ala-Glx- [SEQ ID NO:5] and R"=-Ala-Ala;

R'=Leu-Thr-Ala-Glx- [SEQ ID NO:5] and R"=-Ala-Val.

The peptides of the present invention may be combined in pharmaceutical preparations for a variety of therapeutic uses. The preparations may be administered to a variety of hosts for therapeutic purposes. Suitable hosts include human and non-human primates, domestic animals including dogs, cats, rodents, birds, horses, cows, pigs, fish, and the like.

The compositions may also find use for pre- or post-exposure prophylaxis, e.g., HIV prophylaxis following "dirty needle" injuries to health care workers or routinely accompanying blood transfusions or to persons in danger of becoming exposed to infected body or culture fluids. The peptides of the present invention are particularly useful for augmentation of vaccinations. By "augmentation of vaccines", it is meant that the level and/or duration of complete or partial immunity to an infectious disease resulting from a vaccination procedure is increased.

Administration of the peptides of the present invention in conjunction with a vaccine may increase the immune response to the vaccine providing both a higher level of immunity and/or a longer duration of anamnestic responses. The peptides may be administered prior to, simultaneously with, or following vaccination. Generally, the peptides will be administered prior to or simultaneously with vaccination.

The subject pharmaceutical compositions may be administered by parenteral, topical, oral, or local routes and in either prophylactic and/or therapeutic treatment regimens. Preferably, the subject peptides are administered intramuscularly or intranasally. For administration by the parenteral (i.e., intravenous), subcutaneous, intramuscular, or intrathecal routes thie invention provides pharmaceutical preparations, e.g., a solution of the subject peptide dissolved in a pharmaceutically acceptable carrier, preferably an aqueous carrier. A variety of aqueous carriers may be used, e.g., water, buffered water, 0.4% saline, 0.3% glycine, and the like. Optional additives for increasing stability may be included, e.g., albumin, lipoprotein, globulin, etc., or the subject peptide may be glycosylated to increase stabillity. Pharmaceutical preparations according to the invention may be sterilized by conventional techniques, e.g., irradiation, filtration, and the like. Aqueous solutions according to the invention may be packaged under aseptic conditions or lyophilized, in the latter case the lyophilized preparation being re-combined with a sterile aqueous solution prior to administration. The compositions may optionally contain pharmaceutically acceptable auxiliary substances as required to approximate physiological conditions, such as pH adjusting and buffering agents, tonicity adjusting agents and the like, for example, sodium acetate, sodium lactate, sodium chloride, potassium chloride, calcium chloride, etc.

The subject peptides in the pharmaceutical preparations according to the present invention may be present as free peptides or as water soluble pharmaceutically acceptable salts, e.g. sodium, potassium, ammonium or zinc salts. Pharmaceutical preparations may also include optional physiologically acceptable carriers, and other active ingredients that may be intended to impart other pharmaceutical activities to the composition, e.g., antibiotics, interferon, anesthetics, and the like may be included in the subject pharmaceutical preparations.

The concentration of the subject peptides in pharmaceutical preparations may vary but generally will be in the range of about 0.001% to about 15 or 20% by weight dependent upon fluid volumes, viscosities, etc., and the particular mode of administration desired, e.g. for intramuscular injection a solution of the subject peptide in a therapeutically effective immunopotentiating amount in the range of about 0.001% to 0.01% by weight. When formulated as a tablet capsule or suppository, a preferred pharmaceutical preparation of the subject peptide has about 0.1 mg per tablet, suppository or capsule. The subject capsules, suppositories or tablets may optionally contain an excipient, vehicle or filler, e.g. starch, glucose, etc. Methods for preparing pharmaceutical preparations according to the invention may vary. Preparations for parenteral, oral, and topical administration are known and apparent to those skilled in the art, e.g., as described in detail in "Remington's Pharmaceutical Science", 17th ed., Mack Publishing Company, Easton, Pa. (1985), incorporated herein by reference.

Determining, an effective amount of a subject peptide useful for treating hosts afflicted with an ailment is accomplished using empirical methods known in the clinical arts. For example, delivering an amount of a subject peptide effective to produce immunomodulation in a host may be determined by serial determinations (in time) of leukocyte counts, CD 2-mediated sheep red blood cell rosette formation by T-cells; determining the relative and/or absolute levels of different leukocyte subsets (e.g., CD4 and CD8 subsets of T lymphocytes); measuring erythrocyte sedimentation rate; quantifying serum proteins such as C-reactive protein, immunoglobulin, antigen-specific auto-antibodies (e.g., rheumatoid factor or anti-erythrocyte antibodies), complement levels, and like; as well as by monitoring an organ function in a host (e.g., liver function). Efficacy of a subject pharmaceutical preparation for treatment of an anemia may be monitored e.g. by serial determinations of hematocrit, hemoglobin, mean corpuscular volume, and the like. Methods for monitoring treatment of infection include, e.g., microbiological culture techniques and organ function indices. Treatments of atopic states such as allergy may be evaluated by e.g. determining skin test reactivity or measuring serum IgE levels. Treatments of immune disorders may be monitored by determining e.g. white blood cell counts or by performing in vitro assays measuring leukocyte function. Treatments effective to augment vaccine immunization protocols may be determined by monitoring e.g. by measuring levels of serum antibody produced following vaccination, or by evaluating the incidence of infection in groups of patients following vaccination.

Compositions of the invention may be administered to a host already suffering from an infection in a "therapeutically effective dose", i.e., an amount sufficient to alleviate or at least partially arrest one or more symptoms of the disease or its sequelae. The therapeutically effective dose will of course vary accroding to at least the severity of the disease (or infection) and the age, body weight and general state of health of the subject so treated. Generally the therapeutically effective dose will range from about 0.001 mg/kg to about 5000 mg/kg body weight per day, more commonly the dose will be about 0.1 mg/kg to about 1000 mg/kg body weight per day, usually the dose will be about 0.25 mg/kg to about 100 mg/kg body weight per day, more usually the dose will be about 0.5 mg/kg to about 20 mg/kg body weight per day, and preferably the dose will be about 0.7 mg/kg to about 10 mg/kg body weight per day.

Maintenance dosages delivered over a prolonged period of time will be adjusted as necessary by the attending physician, but will generally be sufficient to keep a subject symptom free. Because of their safety, lack of toxicity and immunogenicity, the subject pharmaceutical preparations of the instant invention may be used for treatments in serious disease states that are life-threatening or potentially life threatening. In the latter cases, a treating physician may feel it appropriate to administer substantial excesses of the subject pharmaceutical preparations, and such uses are considered to lie within the metes and bounds of the instant invention. Also, for veterinary uses it may be desirable to treat certain species of animals with higher doses.

For prophylactic uses, compositions according to the invention are administered to patients at an increased relative risk for developing infection, anemia, or disease. A "prophylactically effective dose" is one that is sufficient to decrease the relative risk of the subject so treated to within a normal range for age, sex, height, weight, and medical history. The amount of the subject pharmaceutical preparation that constitutes a "prophylactically effective dose" will depend at least on the patient's state of health and weight, but is generally within the ranges specified above for therapeutically effective dose. Examples of subjects who may benefit from prophylactic treatments according to the invention include those who are at an increased relative risk of exposure to an infectious disease, e.g., health-care workers, travellers, family members of infected individuals, immunosuppressed cancer patients and the like. The pharmaceutical preparations of the instant invention may also be administered prior to surgery to lessen the risk of infectious complications and restore erythrocyte levels following blood loss.

A treatment regimen may consist of one or more administrations of the subject pharmaceutical preparations with the therapeutically effective or prophylactically effective dose levels being determined empirically by the treating physician or veterinarian. For treatment of infection, the subject pharmaceutical preparations may be administered alone or with e.g., antibiotics, anti-viral compounds, anti-fungal compounds, or anti-parasitic compounds, i.e., as an adjunct to a therapy. When employed in a therapy for immunomodulation, e.g., in a cancer patients, the subject pharmaceutical preparations may be administered with one or more chemotherapeutic agents or other treatment modalities used in cancer therapy. When used in an adjunct therapy, the subject pharmaceutical preparations may be administered either at the same time as other treatment modalities, or separately, i.e., at different time intervals.

The subject peptides of the instant invention are synthesized by techniques known in the peptide art. Generally, the peptides are prepared using solution- or solid-phase peptide synthesis, including Merrifield solid-state peptide synthesis. For example, an amino- and side-chain-protected-derivative of an activated-ester of Glx is reacted with side-group protected L-Lys, i.e., the latter being affixed to a solid phase e.g. through its C-terminus. After elimination of the alpha-amino protecting group, the next amino acid may be added, and so forth for serial additional of other amino acids. The subject peptides are removed from a solid phase using acid hydrolysis aimed at simultaneously removing protective groups. The peptides may then be isolated (e.g. by HPLC), lyophilized, and stored for future use. Suitable techniques of peptide synthesis are described in detail in Stewart and Young, "Solid Phase Peptide Synthesis", 2d edition, Pierce Chemical Company, 1984; and in Tam et al., *J. Am. Chem. Soc.*, 105:6442 (1983), both of which are incorporated herein by reference. Alternatively, recombinant DNA technology may be used to express the desired peptide using transfection or transduction with a vector- or retrovirus to transform a eukaryotic or a prokaryotic host cell according to techniques described e.g. in Maniatis et al., Molecular Cloning, A Laboratory Manual, Cold Spring Harbor Laboratory, 1982, incorporated herein by reference.

Embodiments of the invention provide therapeutic and prophylactic methods for administering to a subject a pharmaceutical preparation containing a peptide having the formula R'-Glx-Lys-R", or its pharmaceutically acceptable salt. In the latter method Glx is Glu or Gln; R' is H or a first amino acid sequence having fewer than 7 amino acids; R" is -H or a second amino acid sequence having fewer than 7 amino acids; and the subject peptide has a sequence of at least 2 and not more than 9 amino acids. A therapeutically effective dose or a prophylactically effective dose of the pharmaceutical preparation peptide is preferably administered. Preferably either Glx-Lys or Thr-Ala-Glx-Glx-Lys [SEQ ID NO:6] are employed in the subject method, and most preferably L-Gln-L-Lys, L-Thr-L-Ala-L-Glu-L-Glu-L-Lys [SEQ ID NO:2], L-Thr-L-Ala-L-Gln-L-Glu-L-Lys [SEQ ID NO:7], or L-Thr-L-Glu-L-Gln-L-Lys [SEQ ID NO:8] are employed in the subject therapeutic method.

Immunomodulation may be one aim in using a subject therapeutic or prophylactic treatment regimen according to the invention. The subject therapy may be effective to either stimulate or depress the immune system in a host so treated.

Immune stimulation may occur following administration of the peptides to immunosuppressed or immunodeficient hosts as evidenced by an increase in either the number of immune cells in blood or tissues, or an increase in one or more functions of immune cells, e.g., as measured using an in vitro assay. The subject pharmaceutical preparations may be used to treat subjects having a primary or secondary immunodeficiency disease, or a disease sequelae of these diseases, e.g., an opportunisitic infection. For example, primary immunodeficiencies, such as the acquired immunodeficiency syndrome (AIDS), DeGeorge's syndrome, severe combined immunodeficiency, and the like, may be treated according to the methods of the invention, e.g. to reduce the relative risk of acquiring an opportunistic infection. Secondary immunodeficiencies, such as anergy from tuberculosis, drug-induced leukopenia, non-HIV viral illnesses leukopenia, radiation poisoning, toxin exposure, malnutrition, and the like, may also be treated according to the methods of the invention. Stimulation of a subject's immune system may aid in the treatment of diseases including, e.g., malignancies, infections, and the like.

In other embodiments the invention provides methods useful for treating patients with autoimmune diseases, allergy and atopic type I hypersensitivity diseases, e.g., atopic dermatitis. Autoimmune states include, e.g., systemic lupus erythematosis, early onset type-I insulin dependent diabetes, rheumatic fever, rheumatoid arthritis, multiple sclerosis, Sjogren's syndrome, Reynards syndrome and the like. The subject therapies may restore a natural regulatory balance to the immune system of a host so treated, and thereby decrease or eliminate, or deviate an ongoing immune reaction directed against host tissues. The subject methods may also be useful in treating opportunistic infections commonly associated with immunosuppressive therapies used in treating autoimmune diseases, e.g., corticosteroid therapy. The latter opportunistic infections may include bacterial, viral, fungal and parasitic infections.

Bacterial infections that may treated according to the methods of the therapeutic and prophylactic methods of the invention include but are not limited to, e.g., mycobacterial infections such as tuberculosis or leprosy, or infection with *M. avium*, or *M. intracellulare;* gram positive infections such as Staphylococal, or Streptococcal infections; gram negative infections such as Pseudomonal infection; mycoplasmal infection such as with *Mycoplasma pneumoniae* (TWAR); spirochetal infection such as syphilis; Pneumocystis, and the like. Both aerobic and anaerobic bacteria may be treated by according to the methods of the present invention.

Viral infections that may be treated according to the therapeutic and prophylactic methods of the invention including but not limited to HIV-1 and HIV-2, cytomegalovirus, herpes simplex virus Type I and Type II, Epstein-Barr virus, HTLV-I and HTLV-II, Marek's disease, hog cholera virus, feline sarcoma virus, distemper virus, and the like.

Fungal infections, that may be treated according to the therapeutic and prophylactic methods of the invention include but are not limited to infections with *Candida albicans* or Cryptococcus, and Histoplasmosis, Coccidiomycosis, and Aspergillosis.

Parasitic diseases that may be treated according to the therapeutic and prophylactic methods of the invention include but are not limited to malaria, schistosomiasis, toxoplasmosis, and leishmaniasis.

Methods for treating infections may be limited to administration of just the pharmaceutical preparations of the invention, or may include the additional administration of a second therapeutic agent, e.g., an antibiotic; or of an anti-viral, anti-fungal or anti-parasitic compound. Skilled practioners will appreciate that selection of an appropriate adjuvant therapy will depend upon the clinical status of the patient. The methods of the invention may produce a desirable clinical effect that allows the dose of the second therapeutic agent, e.g., anti-infective, to be reduced. The methods of the invention thus may provide a means for reducing or eliminating dose-related complications and/or side effects associated with administration of the second therapeutic agent.

The methods of the present invention may also be used to treat atopic states, e.g., atopic allergies such as dermatitis. The peptides of the instant invention may be useful for decreasing or deviating an ongoing immune response, e.g. synthesis of IgE that mediates allergy. "Modulating" is intended to mean increasing or decreasing the magnitude of an immune response and "deviation" is used, as in "immune deviation", to mean a redirecting of an ongoing immune response, e.g. redirected from an immune response directed toward a first antigen to a response directed to a second antigen; or, redirected from production of IgE to production of IgG; or e.g., redirected from a humoral response to a cell-mediated immune response. Immune deviation using the subject pharmaceutical preparations may prove useful for treating diseases e.g. acute allergic reactions, chronic urticaria, atopic dermatitis, and the like.

Immune disorders may also be treated according to the methods of the invention including but not limited to chronic B-cell lymphoma, Hodgkins disease, pre-leukemia, chronic granulomatous disease, Waldenstrom's macroglobulinemia, leukemoid reactions, and the like.

Anemias may also be treated according to the methods of the invention including but not limited to acute hemorrhagic anemia, anemias of chronic disease, megaloblastic anemias, iron deficiency anemias, hemoglobinopathies, and the like.

The methods of the invention may also indirectly enhance wound healing such as by reducing local inflammation or infection in wound sites.

The following Examples are offered by way of illustration and not limitation.

EXAMPLE 1

Effect on Immune System of Healthy Guinea Pigs

Forty male guinea pigs were used in the following test. Most of the animals were treated daily with a single dose (i.m.) of 1 µg/kg Thr-Ala-Glu-Glu-Lys [SEQ ID NO:2] (HM897) on each of five consecutive days. Control animals were treated with single daily doses of 0.5 ml (i.m.) of normal saline.

Test parameters measured in this study included differential blood cell counts, cellular lysosomal cationic protein levels (i.e., a measure of neutrophil activation and nonspecific resistance to infection), "Activated" T-lymphocytes (i.e., T-cell rosetting to trypsinized sheep red blood cells), "Total" $CD2^+$ T-lymphocytes ($E_s$-RFC), C3b-receptor bearing lymphocytes, i.e., B-lymphocytes ($E_s$AC-RFC). The latter parameters were measured for lymphocyte populations in peripheral blood, thymus, lymph nodes, spleen and red bone marrow. Functional tests of peripheral blood lymphocytes included cytokine measurement, i.e., synthesis of Leukocyte Migration Inhibition Factor (LMIF) after in vitro stimulation with Con-A.

Post-treatment histological examination was made to evaluate the effects of HM897 on thymus, lymph nodes, spleen, and red bone marrow.

The preceeding tests and histological evaluations were made on the 10th and 20th days after initiation of the treatment. Eight normal animals constituted the control (normal) group and 12 animals constituted each of the HM897 treated groups (i.e., day 10 and day 20).

The data relating to lymphocyte cell numbers in various immune tissues following treatment is summarized in TABLE 1, below.

TABLE 1

Changes in Immune Cells in Normal Guinea Pigs Treated with HM897

| Treatment | Mean Cell Numbers ($\times 10^3$/mg) | | | | | | | | Peripheral Blood | | | | | |
|---|---|---|---|---|---|---|---|---|---|---|---|---|---|---|
| | Thymus | | Spleen | | Lymph Nodes | | Bone Marrow | | PBL | Differential Cell Counts (%) | | | | |
| (days)[a] | T | B | T | B | T | B | T | B | ($\times 10^9$/ml) | PMN (%) | Lym. (%) | Mono (%) | Baso (%) | Eos. (%) |
| Normal (X ±) | 352 ± | 3 ± | 59 ± | 89 ± | 102 ± | 127 ± | 26 ± | 45 ± | 8.7 ± | 44 ± | 51 ± | 3.6 ± | 0.7 ± | 0.3 ± |
| (S.D.) | 178 | 3 | 39 | 17 | 59 | 31 | 12 | 7 | 2 | 5 | 9 | 1.1 | 0.4 | 0.2 |
| HM897 (10 d) | 627 ± | 2 ± | 46 ± | 265 ± | 94 ± | 214 ± | 32 ± | 35 ± | 13.0 ± | 48 ± | 46 ± | 2.3 ± | 1.0 ± | 0 ± |
| (X ± S.D.) | 47* | 0.2* | 8 | 17* | 9 | 21 | 5* | 4* | 1.3 | 5 | 4 | 0.6 | 0.1 | 0 |
| Increase (%): | 78 | −33 | −24 | 198 | −7 | 70 | 19 | −32 | 49 | 9 | −10 | −36 | 43 | −100 |
| HM897 (20 d) | 790 ± | 7 ± | 104 ± | 391 ± | 131 ± | 368 ± | 63 ± | 117 ± | 10.1 ± | 47 ± | 52 ± | 1.3 ± | 0.5 ± | 0.04 ± |
| (X ± S.D.) | 79* | 1* | 22 | 3* | 21 | 29* | 5* | 13* | 1.9 | 6 | 3.4 | 0.4 | 0.1 | .01 |
| Increase (%): | 124 | 233 | 78 | 338 | 27 | 191 | 162 | 164 | 14 | 2 | 2 | −64 | −100 | 0 |

[a].) Increase = (HM897 − Normal)/(Normal) × 100%; Normal = mean ± S.D. of all saline treated control animals (n = 32); na, not applicable; *, statistically significant difference in comparison with the respective 10 day or 20 day control values.

The results presented in TABLE 1, illustrate the effects of administering the HM897 peptide daily over the course of 5 days on the numbers of T- and B-lymphocytes in peripheral blood and in different lymphoid organs on day 10 and day 20. It is noteworthy, that despite the absence of a bulk change in the populations of cells in peripheral blood (PBL; differential counts), the HM897 peptide stimulated increases in T- and B-lymphocytes in lymphoid organs. In the case of the thymus, the number of T-lymphocytes increased by 1.24-fold by day 20, and in spleen B-lymphocytes increased by 3.38-fold by day 20. Histological examination at day 10 and day 20 suggested increased proliferation and differentiation of lymphoid cells in thymus and bone marrow, an observation supported by the observed 1.62-fold and 1.64-fold increases in T- and B-lymphocytes, respectively, in bone marrow at day 20 (TABLE 1). On day 10 histological examination also revealed increased mitotic activity in lymph nodes and spleen. In this study peripheral blood lymphocyte function, as assessed by LMIF cytokine, was not significantly different after treatment of normal guinea pigs with HM897. Neutrophil activation (i.e., lysosomal cations) were also not significantly different than control at day 10 or day 20.

measured in peripheral blood and in thymus, spleen, lymph nodes, and bone marrow on the 8th and 21st days after the irradiation. The experiment was repeated three times. Illustrative effects of HM897 treatments on the populations of immune cells in various lymphoid organs are shown in TABLE 2, i.e., illustrative results of two (of the three) experiments are presented.

TABLE 2

Changes in Lympocyte Cell Numbers in Lymphoid Tissues of Guinea Pigs Following Irradiation and Treatments for 8 or 21 Days with HM897

| Treatment (days)[a] | Mean Cell Numbers ($\times 10^3$/mg) | | | | Mean Cell Numbers ($\times 10^3$/mg) | | | |
|---|---|---|---|---|---|---|---|---|
| | Thymus | Spleen | Lymph Nodes | Bone Marrow | Thymus | Spleen | Lymph Nodes | Bone Marrow |
| Non-Irradiated (8d) (X ± S.D.) | 578 ± 40 | 401 ± 44 | 258 ± 23 | 572 ± 44 | 416 ± 28 | 62 ± 5 | 72 ± 8 | 18 ± 1 |
| Irradiated (8d) (X ± S.D.) | 277 ± 21 | 365 ± 28 | 181 ± 15 | 592 ± 51 | 92 ± 8* | 31 ± 5 | 24 ± 2* | 36 ± 4* |
| 8d Lym. Drop (%): | 52 | 9 | 30 | −3 | 78 | 50 | 67 | −100 |
| HM897 (8 d) (X ± S.D.) | 234 ± 55* | 322 ± 49 | 351 40** | 393 ± 35* | 195 ± 11* | 60 ± 6** | 60 ± 9** | 14 ± 3** |
| 8d HM897 Increase (%): | −15 | −12 | 94 | −34 | | 50 | 150 | −61 |
| Non-Irradiated (21d) (X ± S.D.) | 570 ± 42 | 476 ± 38 | 270 ± 29 | 613 ± 60 | 307 ± 32 | 69 ± 5 | 71 ± 8 | 21 ± 2 |
| Irradiated (21d) (X ± S.D.) | 290 ± 32 | 468 ± 31 | 58 ± 2 | 953 ± 84 | 174 ± 19* | 67 ± 7 | 0.5 ± 0.03* | 10 ± 1* |
| 21d Lym. Drop (%): | 49 | 2 | 79 | −55 | 43 | 3 | 99 | 52 |
| HM897 (21 d) (X ± S.D.) | 1213 ± 106* | 353 ± 41 | 586 ± 70* | 649 ± 44** | 897 ± 49* | 82 ± 12 | 89 ± 12** | 19 ± 1** |
| 21d HM897 Increase (%): | 318 | −25 | 910 | −32 | 416 | 22 | 17700 | 90 |

[a].) Lym. Drop = (Non-Irradiated - Irradiated)/(Non-Irradiated) × 100%; Increase = HM897 - Irradiated)/(Irradiated) × 100%;
*, statistically significant decrease in comparison with the respective 8 day or 21 day non-irradiated control values;
**, statistically significant increase in comparison with the respective 8 day or 21 day irradiated control values

EXAMPLE 2

HM897 Treatment of Primary Immunodeficiency: Irradiated Guinea Pig Animal Model

Guinea pigs (250–300 gm) were X-irradiated at a total body dose of 1 Gy using a target-to-skin distance of 70 cm, a time of exposure of 2 minutes 48 seconds, and an RUM-17 irradiator with parameters set at: 180 kV; 15 mA; 0.5 Cu filter; 1 Al; and, dose output 35.8 P/min. HM897 treatments were administered to animals in the experimental group (n=8) on a daily baisis i.m. as a single 1 μg/kg dose beginning on the day following the irradiation. Animals in the irradiated control group (n=12) were treated using the same regimen but with normal saline 0.5 ml i.m., instead of HM897. Twelve non-irradiated normal animals served as normal treatment vehicle-controls and they were treated with saline only on the same treatment regimen (non-irradiated control). Leukocyte and lymphocyte levels were Properties of the Primary Immunodeficiency Animal Model: The results presented in TABLE 2 show a statistically significant drop in lymphocyte counts in thymus and spleen at day 8 that decreased somewhat by day 21. The latter drop was accompanied by a significant drop in lymphocyte counts in lymph nodes that increased from day 8 to day 21. Lesser (not significant) changes were observed in the differential cell counts and total numbers of immune cells in peripheral blood of the irradiated animals.

HM897 Treatments: The results presented in TABLE 2 show that treatments with HM897 increased the number of lymph nodes lymhocytes at day 8 (i.e., by 94%–150%) that were 9–18 times greater at day 21 than those present in the control irradiated animals. In addition, at day 21 significantly increased lymphocyte counts were observed in thymus, i.e. 3–4 fold increased relative to irradiated controls, and about 2-fold higher than saline-treated non-irradiated animals.

Principal Findings of Histologic Studies: Treatments with the HM897 peptide appeared to stimulate proliferation of lymphocytes in lymphoid tissues. In controls there was no apparent restoration of immune cells in lymphoid tissues at the observation points.

Leukocyte Function Tests: Lysosomal cation levels in neutrophils (a measure of neutrophil activation) were not significantly increased in irradiated HM897 treated animals relative to irradiated controls. Production of LMIF in response to stimulation with either Con-A or PHA were also not significantly different. Levels of "Active" T-lymphocytes (i.e., T-cells rosetting with trypsinized $E_s$) and total T-lymphocytes (E-RFC) were also not significantly different.

T-lymphocytes (E-RFC), and B-lymphocytes (EAC-RFC) in blood, thymus, lymph nodes, spleen and bone marrow.

The experiments were repeated three times and the results recorded in 2 different experiments are summarized in TABLE 3, below.

TABLE 3

Changes in Lymphocyte Numbers in Lymphoid Tissues of Guinea Pigs Following Thymectomy and 15 Days of Treatments with HM897

| Treatment[a] | Mean Cell Numbers (× $10^3$/mg) | | | Mean Cell Numbers (× $10^3$/mg) | | |
|---|---|---|---|---|---|---|
| | Spleen | Lymph Nodes | Bone Marrow | Spleen | Lymph Nodes | Bone Marrow |
| Sham-Thymectomy (X ± S.D.) | 84 ± 9 | 33 ± 2 | 12 ± 2 | 96 ± 6 | 61 ± 6 | 3 ± 0.3 |
| Thymectomy (X ± S.D.) | 84 ± 7 | 48 ± 3 | 8 ± 1* | 82 ± 4 | 30 ± 2* | 4 ± 0.5* |
| Lym. Drop (%): | 0 | −45 | 33 | 15 | 51 | −33 |
| Thymectomy + HM897 | 48 ± 4** | 32 ± 3** | 9 ± 1 | 46 ± 4** | 28 ± 2* | 6 ± 0.4* |
| HM897 Increase | −43 | −33 | 13 | −44 | −7 | 50 |

[a].) Lym. Drop = (Sham Thymx. - Thymx.)/(Sham. Thymx.) × 100%;
Increase = (HM897 - Thymx.)/Thymx.) × 100%;
*, statistically significant decrease in comparison with the sham-operated control values;
**, statistically significant increase in comparison with the thymectomized control values.

Summary: The combined results suggest that HM897 acts to stimulate proliferation and/or maturation of lymphocytes in the lymphoid organs or irradiated subjects without directly activating lymphocytes (or neutrophils) in peripheral blood.

EXAMPLE 3

Effects of HM897 in an Animal Model of Secondary Immunodeficiency: Thymectomized Guinea Pigs Model: Adult thymectomy results in an immunodeficiency state in which cell mediated immune responses and humoral antibody reponses to T-dependent antigens are defective Thymectomized Animals: Twenty adult outbred male juvenile guinea pigs (1 month of age; 130–150 gm) were thymectomized and 3 months later treatments with HM897 were initiated. (Four animals were lost prior to infection before treatments could be initiated.)

Sham-Thymectomy Controls: Ten juvenile outbred guinea pigs were sham-thymectomized. (One animal was lost to post-surgical complications.)

Treatment Group: HM897 was administered i.m. as a single daily dose of 1 mg/kg to 8 thymectomized animals on each of 10 consecutive days.

Thymectomized Controls: Normal saline 0.5 ml was administered i.m. as a single daily dose on each of 10 consecutive days to 8 thymectomized animals.

Sham-Thymectomy Controls: Normal saline 0.5 ml was administered i.m. as a single daily dose on each of 10 consecutive days to 9 sham-thymectomized animals.

Parameters Tested: Test parameters were determined on the 15th day after onset of the control (saline) or HM897 treatments. Parameters included differential blood counts and determinations of "active" T-lymphocytes, total The results presented in TABLE 3 indicate the HM897 treatments increased the number of lymphocytes in bone marrow of thymectomized animals, and decreased lymphocyte cell counts in spleen and lymph nodes (presumably by mobilizing those cells into peripheral blood and other lymphoid tissues such as Peyers patches). The combined results presented in TABLE 1–3 suggest that HM897 treatments may stimulate production of lymphocyte precursors in bone marrow, that can effectively home to lymphoid tissues and differentiate and mature into T- and B-lymphocyte subsets, if tissues are present. In thymectomized animals, T-lymphocytes are known to home in small numbers to the spleen, but in fewer numbers than with a normal animal. Thus, the observed build-up of lymphocytes in bone marrow (TABLE 3) may reflect stimulation of T-lymphocyte proliferation, but without the thymus the cell remain in the bone marrow.

EXAMPLE 4

Effect of HM897 Treatments on Expression of T- and B-Lymphocyte Cell Surface Receptors and Markers Thymus-Derived T-Lymphocyte Cell Surface Receptors:

In vitro studies were conducted to evaluate the effects of HM897 on expression of T- and B-lymphocyte cell surface receptors, i.e., CD2 receptors ($E_s$-RFC; $E_r$-RFC) capable of participating in co-stimulant pathways of T-lymphocyte activation, and cell surface Ig, IgM, IgG, and IgA, (markers for B-lymphocyte maturation).

Trypsin treatment of T-lymphocytes removes cell surface CD2-receptors for heterologous red blood cells, i.e., the guinea pig T-lymphocyte receptor for rabbit red blood cells ($E_r$). Following trypsinization partial recovery of CD 2 can be effected by incubating the cells in vitro at 37° C. for several hours time to allow synthesis and cell surface expression of CD 2. The effects of HM897 on recovery of thymocyte $E_r$-receptors was investigated. Thymocytes from guinea-pig were trypsinized ($10^7$ cells/ml in a final 0.125% trypsin solution) and then their rosette-forming capacity with rabbit erythrocytes ($E_r$-RFC; 1% solution by volume)

was evaluated. The cells were incubated with the HM897 peptide at concentrations of 1, 10 and 100 μg/ml in tissue culture medium. Rosetting was determined by centrifuging T-cells together with $E_r$ using low speed (800 rpm×5 minutes), and then resuspending the cell pellets and determining microscopically the percentage of rosette forming cells. The positive control consisted of intact thymocytes (not trypsinized) and the negative control was trypsinized-thymocytes incubated in only tissue culture medium (i.e., no peptide).

TABLE 4

HM897 Up-Regulates Expression of
T-Lymphocyte Cell Surface Receptors

| Trypsin-Treated | Recovery Treatment | Mean % ± S.D. $E_r$-RFC |
|---|---|---|
| − | None | 73 ± 2 |
| + | None | 38 ± 2* |
| + | 1 μg/ml HM897 | 63 ± 2** |
| + | 0.01 μg/ml HM897 | 68 ± 2** |
| + | 00001 μg/ml HM897 | 48 ± 5 |

*statistically significant decrease (p < 0.05) in comparison with non-trypsin-treated control;
**statistically significant increase (p < 0.05) in comparison with trypsin-treated control.

The results presented in TABLE 4 indicate that HM897 upregulated expression of $E_r$ receptors (i.e., CD 2) on trypsinized thymocytes with a maximal effect being observed at 0.010 μg/ml with restoration of CD 2 receptor function on 68% of the trypsin-treated cells. The mechanism (s) responsible for these observed effects on thymocytes may involve: cell surface expression of molecules from within a preformed pool of CD 2 receptors; or, upregulation of synthesis and cell surface expression of receptors synthesized de novo; or, increasing the binding affinity (avidity) of non-damaged cell surface CD 2 receptors, i.e., allowing fewer receptors to perform more effectively in rosetting; or, stabilization of CD 2-ligand interactions.

Human B-Lymphocyte Cell Surface Markers:

Patients with chronic streptococcal and staphylococcal infection may exhibit secondary immunodeficiency (i.e., decreased immune responsiveness to other infectious agents) as a result of the effects of bacterial products such as Staphylococcal Protein A and streptolysins on immune cells. In the present study peripheral blood was obtained from 5 patients being followed with pustular cutaneous streptococcal and staphylococcal lesions and altered peripheral blood lymphocyte cell counts.

Peripheral blood was obtained from patients with streptococcal and staphylococcal skin disease and lymphocytes prepared by Ficoll-Hypaque density sedimentation according to the method of Boyum. The percentage of lymphocytes bearing cell surface immunoglobulin (SIg+), IgM, IgG, and IgA were determined by imunofluorescence microscopy using FITC-conjugated isotype-specific antibodies. Cell surface expression of immunoglobulin markers on B-lymphocytes was determined before and after incubation in vitro with HM897 at a concentration of 1 μg/ml in tissue culture medium. The results are presented in TABLE 5, below.

TABLE 5

HM897 Up-Regulates Expression of
B-Lymphocyte Cell Surface Markers

| In Vitro Treatment | Mean % ± S.D. | | | |
|---|---|---|---|---|
| | SIg⁺ | IgM⁺ | IgG⁺ | IgA⁺ |
| None | 8.5 ± 0.6 | 4.6 ± 0.6 | 4.9 ± 0.5 | 0.7 ± 0.4 |
| 1 μg/ml HM897 | 15.5 ± 0.8* | 6.8 ± 0.2* | 6.8 ± 0.6* | 2.5 ± 0.8* |

*statistically significant increase (p < 0.05) in comparison with non-treated control.

The results presented in TABLE 5 show that in vitro treatments with HM897 significantly upregulated cell surface expression of B-lymphocyte marker immunoglobulins on lymphocytes from patients with secondary immunodeficiency. For comparison, the mean value (±S.D.) for SIg⁺-lymphocytes is 17.8±3.3 in the peripheral blood of normal healthy volunteers. In vitro treatment with HM897 at 1 μg/ml increased the percentage of SIg⁺-lymphocytes to within the normal range. Expression of surface immunoglobulins on B-lymphocytes is a marker for maturation of the cells and is correlated, in studies with experimental animals, with ability of B-lymphocytes to respond to challenge with foreign antigens.

EXAMPLE 5

Erythropoietic Effects

These studies were designed to evaluate possible erythropoietic effects of HM897 in two different anemia models: namely, an acute hemorrhagic anemia and a hemolytic anemia. Acute hemorrhagic blood loss was modeled by retroorbital bleeding of Balb/c mice. Hemolytic anemia was modeled in CBA mice by using phenylhydrazine hydrochloride at a dose of 120 mg/kg.

In both animal models, HM897 therapy was administered by 5 daily ip injections of peptide at a dose of either 100 μg/kg or 150 μg/kg with the injections commencing 3 hours after induction of acute hemorrhagic blood loss, and 1 day after induction of hemolytic anemia. Test parameters recorded at 3 hrs. and then daily) included measurements of packed red blood cells (i.e., hematocrit); cell counts of leukocytes, erythrocytes, and platelets; and determination of blood hemoglobin levels.

In the hemorrhagic anemia model the greatest change in blood parameters was observed at day 4–5, with erythrocyte count dropping to $4.2 \times 10^6$/ml compared to the pre-treatment mean value of $6.2 \times 10^6$/ml. At the same time the number of platelets increased 3-fold and the number of leukocytes also increased. In contrast, HM897 treated animals total erythrocytes on day 6 exceeded those in control animals (i.e., 6.7 and $7.1 \times 10^6$/ml, respectively for the two different doses of HM897; p<0.05). In support of these measurements, Hemoglobin values (g/dL) were also restored to normal more rapidly in HM897 treated animals than in the controls. Interestingly, in other studies HM897 administered at doses of 0.1 μg/kg–10 μg/kg, i.e., within the range effective to stimulate myelogenous precursors in bone marrow and lymphoid cells in the periphery, was ineffective in stimulating erythropoietic activity.

In the model of hemolytic anemia induced with phenylhydrazine, maximal anemia was manifest at day 7 with erythrocytes decreasing to $3.8 \times 10^6$/ml, platelets falling to just 15% of pre-treatment values and hemoglobin also fell by 15% from pre-treatment levels. In contrast, HM897 treated animals exhibited a mean erythrocyte count of $7.2 \times 10^6$/ml at day 3 (1.7-fold greater than the untreated control).

These combined findings indicate that the dosage and timing of delivery of HM897 to a subject in need thereof can determine whether the peripheral lymphoid system is stimulated, or alternatively, whether bone marrow myelogenous activity and/or erythrogenic activity is stimulated. Monitoring peripheral blood differential cell counts, hematocrit, erythrocyte counts, and numbers of immature myeloid cells in circulation (e.g., CD 34$^+$ cells) allows the dosage level of HM897 to be adjusted to achieve a desired result.

EXAMPLE 6

Effect of HM897 Treatments on Bone Marrow Function in Immunosuppressed Mice and Effects on Bone Marrow M-CFU and GM-CFU Effects of HM897 on Bone Marrow and Peripheral Blood Cell Populations in Imunosuppressed Mice:

The effects of HM897 on bone marrow hematopoietic activity was investigated in 5-fluorouracil (5-FU) immunosuppressed CBA mice. Mice were treated with a dose schedule of 5-FU (i.e., 175 mg/kg, ip, single dose) determined empirically to be sufficient to decrease the absolute number of bone marrow cells and peripheral blood leukocytes by about 50% by day 10–14. Immunosuppression was initiated by ip injection of 5-FU on day −4, and HM897 treatment was administered daily for five days (i.e., days 0 to +5) with a dose of 10 μg/kg being administered ip on each of those days. Differential cell counts were performed using total bone marrow and peripheral blood cell populations collected on day +6. The results are presented in TABLE 6, below.

The results presented in TABLE 6 show that the 5-FU dose schedule reduced the total number of all precursor cell types in the bone marrow except myeloblasts and promyeloblasts, and the results presented in TABLE 7, below, show that peripheral blood leukocytes were reduced to 44% of normal. Comparing the cell populations from HM897-treated animals with those in the control (5-FU) group (TABLE 6, above), for bone marrow the treatments with HM897 resulted in: i) an increase in the numbers of myelokaryocytes, myelocytes/neutrophils, stab and segmented neutrophils, and megakaryocytes; ii) no marked changes in the total numbers of reticular cells, monocytes, myeloblasts, erythroblasts, and erythroid cells; and, iii) a decrease in the absolute numbers of eosinophils, and lymphocytes.

Comparing the cell populations from HM897-treated animals with those in the control (5-FU) group (TABLE 7, below), for peripheral blood the treatments with HM897 resulted in: namely, i) the total number of leukocytes and neutrophils increased (i.e., in parallel with the observed increase in bone marrow neutrophil precursors, TABLE 6); ii) the absolute number of monocytes dropped slightly, but insignificantly, since the percentage of monocytes in peripheral blood was about 2–3% before and after treatment; and, iii) the total number of peripheral blood lymphocytes decreased to within the normal range (as did the number in bone marrow, TABLE 6).

TABLE 6

Effects of HM897 Treatments on Bone Marrow Cell Populations in 5-FU Immunosuppressed CBA Mice.

| Cell Type | Normal Control (untreated) | Negative Control (5-FU only) | Experimental (5-FU + HM897 Therapy) |
|---|---|---|---|
| Myelokaryocytes: ($\times 10^6$): | 2.44 | 1.38 | 2.37 |
| Reticular cells: %: | 0.8 | 0.6 | 0.5 |
| Non-differentiated blast cells: %: | 2.0 | 2.3 | 1.7 |
| Myeloblasts: %: | 3.9 | 6.7 | 4.0 |
| $10^3$/mg: | 95.3 | 92.4 | 98.0 |
| Myelocytes + Neutrophil %: | 5.8 | 3.4 | 5.6 |
| Metamyelocytes: $10^3$/mg: | 141.5 | 46.9 | 137.2 |
| Stab + Seg. neutrophils: %: | 41.9 | 13.1 | 43.8 |
| $10^3$/mg: | 1022 | 181 | 1073 |
| Eosinophils: %: | 1.0 | 1.4 | 0.8 |
| $10^3$/mg: | 24.4 | 19.3 | 19.6 |
| Lymphocytes: %: | 28.8 | 52.5 | 28.0 |
| $10^3$/mg: | 703 | 718 | 686 |
| Monocytes: %: | 2.4 | 3.0 | 3.1 |
| $10^3$/mg: | 58.5 | 41.4 | 76 |
| Megakaryocytes: %: | 0.4 | 0.2 | 0.3 |
| $10^3$/mg: | 46.4 | 31.7 | 41.6 |
| Erythroblasts: %: | 1.9 | 2.3 | 1.7 |
| $10^3$/mg: | 46.4 | 31.7 | 41.6 |
| Erythroid cells: %: | 9.4 | 9.9 | 9.1 |
| $10^3$/mg: | 229 | 137 | 223 |

TABLE 7

Peripheral Blood Leukocyte Populations in
5-FU Immunosupressed CBA Mice Treated with HM897

| Cell Type | Normal Control (untreated) | Negative Control (5-FU only) | Experimental (5-FU + HM897 Therapy) |
|---|---|---|---|
| Peripheral Blood Leukocytes: | 5.72 ± 0.48 | 2.51 ± 0.17 | 6.01 ± 0.6 |
| Total Cells × $10^9$/L: | (100%) | (44%) | (105%) |
| (% of Normal Control Value): | | | |
| Lymphocytes: %: | 47.3 ± 4 | 83.8 ± 6* | 42.0 ± 4** |
| Total Cells × $10^9$/L: | 2.71 ± 0.25 | 2.05 ± 0.14* | 2.57 ± 0.19** |
| (% of Normal Control Value): | (100%) | (78%) | (95%) |
| Stab. Neutrophils: %: | 16.1 ± 0.8 | 3.7 ± 0.2* | 18.6 ± 1** |
| Total Cells × $10^9$/L: | 0.92 ± 0.1 | 0.09 ± 0.01* | 1.12 ± 0.11** |
| (% of Normal Control Value): | (100%) | (10%) | (122%) |
| Segmented Neutrophils: %: | 33.9 ± 4 | 3.3 ± 0.4* | 35.8 ± 4** |
| Total Cells × $10^9$/L: | 1.93 ± 0.2 | 0.08 ± 0.01* | 2.22 ± 0.19** |
| (% of Normal Control Value): | (100%) | (4%) | (115%) |
| Monocytes: %: | 1.86 ± 0.3 | 3.35 ± 0.44* | 2.01 ± 0.16** |
| Total Cells × $10^9$/L: | 0.11 ± 0.01 | 0.08 ± 0.01* | 0.12 ± 0.02** |
| (% of Normal Control Value): | (100%) | (73%) | (109%) |
| Eosinophils: %: | 0.2 ± 0.04 | 0.2 ± 0.02 | 0.11 ± 0.02** |
| Total Cells × $10^9$/L: | 0.01 ± 0.01 | 0.01 ± 0.01 | 0.01 ± 0.01 |
| (% of Normal Control Value): | (100%) | (100%) | (100%) |
| Blast Cells: %: | 0 | 5.2 ± 0.7* | 0 |
| Total Cells × $10^9$/L: | 0 | 0.13 ± 0.04* | 0 |

It is noteworthy that treatments with HM897 were observed to increase *** the numbers of bone marrow megakaryocytes and neutrophils and also peripheral blood neutrophils, since these changes may provide an immunosuppressed subject an increased number of peripheral blood platelets and an increased measure of innate resistance to infection.

Bone Marrow Colony Forming Activity of HM897:

The possible effects of HM897 on bone marrow hematopoetic activity was investigated by culturing guinea pig bone marrow cells in vitro in soft agar and counting monocytic and granulocytic colonies (colony forming units, CFU). The results are presented in TABLE 8.

TABLE 8

Stimulation of Monocytic and Granulocytic Bone Marrow
Colony-Forming Precursor Cells by HM897 In Vitro

| Treatment Group | CFU Type | Mean Number of Colonies ± S.D. | |
|---|---|---|---|
| | | Small Colonies | Large Colonies |
| Normal Control | M-CFU | 11.9 ± 0.9 | 7.4 ± 0.7 |
| HM897 1 μg/ml | M-CFU | 37.8 ± 2.6* | 13.9 ± 1.8* |
| Increase over Control: | | 3.18 | 1.88 |
| | | Clusters | Colonies |
| Normal Control | GM-CFU | 95.1 ± 8.5 | 37.9 ± 3.6 |
| HM897 1 μg/ml | GM-CFU | 118 ± 9** | 40 ± 3.5** |
| Increase over Control | | 1.24 | 1.06 |

*statistically significant difference in comparison with the normal control CFU values.

The results presented in TABLE 8 show about a 2- to 3-fold increase in monocytic CFU's (M-CFU) and a lesser but sigificant increase in granulocytic/monocytic CFU's (GM-CFU) of about 10–20%.

EXAMPLE 7

Effects of Glu-Lys Dipeptide in a Model of Systemic Infection

Preparations of the dipeptide Glu-Lys (EK) were evaluated in a model of systemic infection, i.e., systemic bacterial infection leading to septic shock. Mice were inoculated ip with lethal doses of methicillin-resistant *Staphylococcus aureus*. Treatments with the EK dipeptide preparation were shown, below, to markedly enhance survival.

Balb/c mice were inoculated ip with 10 -$LD_{50}$ doses of ampicillin-resistant *Staphylococcus aureus* suspended in a brain-heart infusion broth that contained 5 percent mucin. To simulate use of EK in as an adjunct to antibiotic therapy, Ampicillin was administered at a dose of 100 mg/kg s.c., i.p., or p.o., one hour following the bacterial inoculation. The clinical response to therapy was determined by monitoring survival in the post-challenge period, i.e., over the three day following bacterial inoculation. In this animal model, where survival permitted (i.e., >50 percent survival), the minimum effective dose (MED) of the EK dipeptide was determined. (Previous studies using methicillin-resistant *S. aureus* (MR) in this animal model revealed that Ampicillin was much less effective when administered sc after the bacterial challenge: i.e, the MED of Ampicillin was >100 mg/kg when it was administered s.c. an hour after the bacterial challenge.)

Two control groups were included in the study. First, the therapeutic efficacy of the EK dipeptide preparation was evaluated (EK control) in a single agent protocol where EK was administered prophylactically prior to bacterial challenge, (i.e., no antibiotic was administered to animals in this group). The number of survivors at 72 hours was determined. Second, saline was administered prophylactically (negative control), and then within one hour of the bacterial challenge Ampicillin was administered i.p. at its MED (i.e., no EK dipeptide was administered to animals in this group). The number of survivors at 72 hours was recorded.

The effect of treatments with the EK dipeptide preparation on survival of animals treated in single agent therapy (i.e., only EK dipeptide) or in a combination therapy with Ampicillin (i.e., EK+Ampicillin), was determined as follows: namely, EK was administered in a prophylactic treatment regimen protocol to all animals except the control groups receiving saline alone or ampicillin and saline. EK was tested at 10, 100, and 1000 μg/kg administered as a single daily i.p. dose on each of 3 consecutive days, a time period normally sufficient to result in lethality of all untreated control animals. Mortality was determined at 12, 24, 36, 48, and 72 hours.

Combination therapy with EK and Ampicillin was also tested in a prophylactic treatment regimen where EK was administered first and then 15 hour later Ampicillin was administered and the bacterial challenge inoculum was injected. Mortality was determined at 12, 23, 36, 48, and 72 hours. The graphically depiction in FIG. 1 illustrates the design of the experimental protocol.

Injection ip of a of a dose of *S. aureus* equivalent to 10 LD50 doses resulted in rapid development of acute peritonitis and easily visible deterioration of the animals condition. Mortality in the control group recieving saline was 100%. For comparative purposes, efficacy of the EK treatment was determined by statistical comparison to control animals treated with either saline alone or Ampicillin and saline.

Microbiological culturing of bacteria with different amounts of the EK dipeptide determined that EK exhibits no anti-microbial activity up to a dose that was calculated to be 1000-times greater than that administered to the animals in this study.

Figure 2:
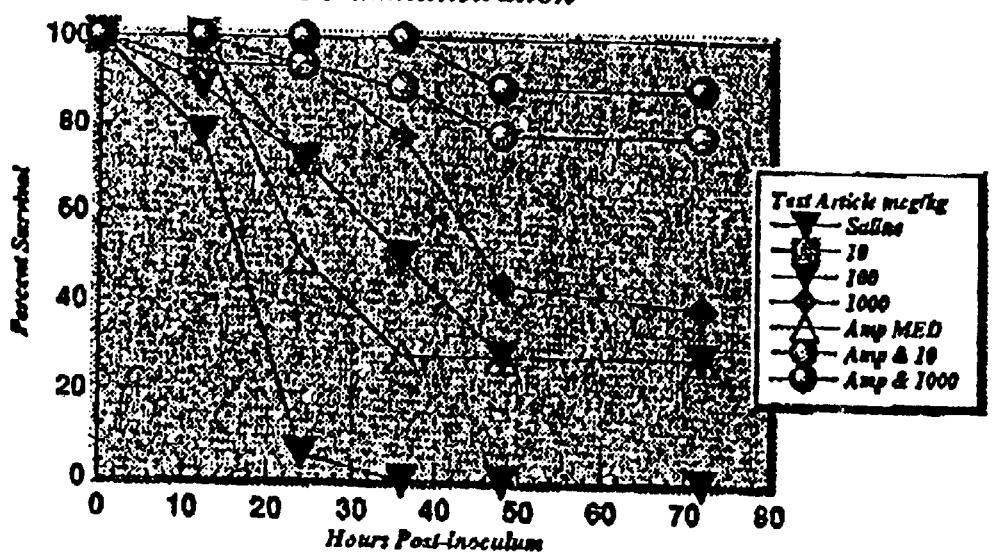
FIG. 2 illustrates survival of bacterially-infected mice treated with EK with and without an adjuvant antibiotic.

The results are summarized in TABLES 9–13. Animals treated prophylactically with EK were protected from subsequent bacterial challenge with *S. aureus*. In the saline control group mortality was 100% at 24 hours. In marked contrast, as many as 78% of the EK treated groups survived at 36 hours. The effect of coadministration of Ampicillin with the EK dipeptide resulted in at least 88% survival at 36 hours compared to only 28% survival if Ampicillin was administered alone, (i.e., coadministration of EK with Ampicillin apparently augmented the action of Ampicillin). The results graphically depicted in FIG. 2 show the results of coadministration of EK with Ampicillin. At 72 hours 27% of the animals receiving only EK were still alive, and 77% were alive in the groups of animals treated with both Ampicillin and EK.

Figure 3:
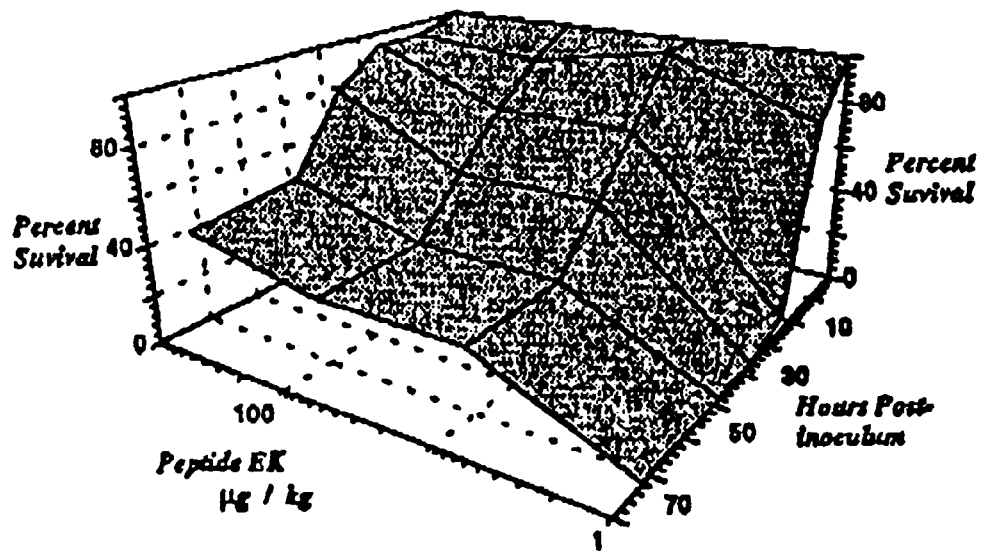
FIG. 3 illustrates survival of bacterially-infected mice treated with EK without adjuvant antibiotics.
Figure 4:
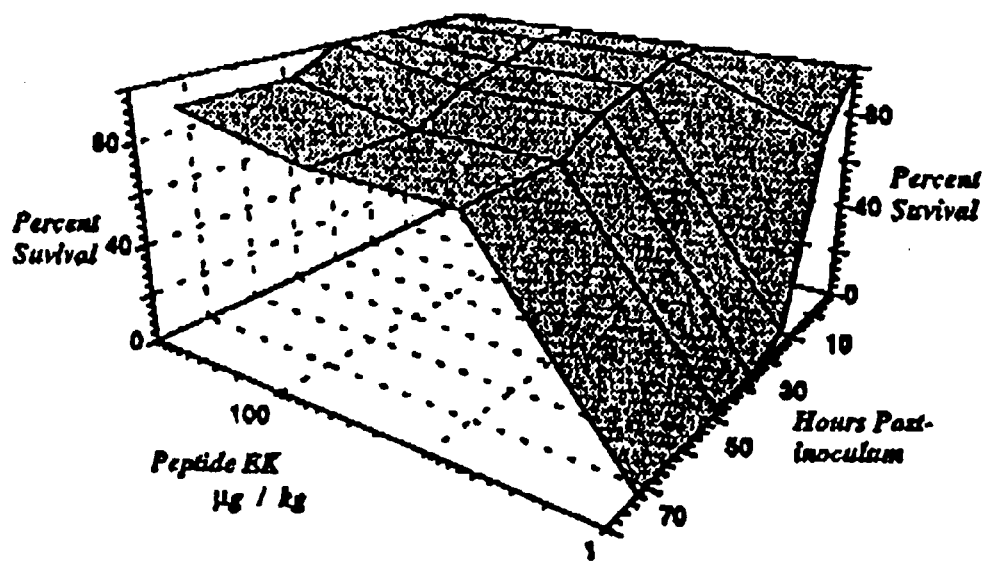
FIG. 4 illustrates survival of bacterially-infected mice treated with EK with adjuvant antibiotics.

The results show that treatment with EK dramatically reduced the mortality resulting from a lethal i.p. dose of *S. aureus*. Moreover, the administration of Ampicillin to mice pre-treated with EK resulted in a 3-fold increase in survival as compared with Ampicillin alone or EK alone. The survival statistics recorded in this study are summarized in TABLES 9–13, below. FIGS. 3 and 4 graphically depict the results of the experiment showing efficacy of EK treatments in systemic bacterial infections.

TABLE 9

Survival Statistics: 12 Hours After Challenge with *S. aureus**

| Test article | Dose (mcg/kg) | Total | Deaths | Survivors | Survival (%) | Chi-square statistics compared to: Control | AA | CD |
|---|---|---|---|---|---|---|---|---|
| Control | — | 18 | 4 | 14 | 77.78 | — | — | — |
| EK | 10 | 18 | 0 | 18 | 100.00 | $P < 0.05$ | n/s | — |
| EK | 100 | 18 | 2 | 16 | 88.89 | n/s | n/s | — |
| EK | 1000 | 18 | 1 | 17 | 94.44 | n/s | n/s | — |
| Amp | MED | 18 | 0 | 18 | 100.00 | $P < 0.05$ | — | — |
| EK + Amp | 10 | 18 | 0 | 18 | 100.00 | $P < 0.05$ | n/s | n/s |
| EK + Amp | 100 | 18 | 0 | 18 | 100.00 | $P < 0.05$ | n/s | n/s |
| EK + Amp | 1000 | 18 | 0 | 18 | 100.00 | $P < 0.05$ | n/s | n/s |

* n/s: not statistically significant; "Control", saline treated; "AA", ampicillin treated; "CD", comparison of EK + Amp with the corresponding dose of EK only.

TABLE 10

Survival Statistics: 24 Hours After Challenge with *S. aureus**

| Test article | Dose (mcg/kg) | Total | Deaths | Survivors | Survival (%) | Chi-square Statistics compared to: Control | AA | CD |
|---|---|---|---|---|---|---|---|---|
| Control | — | 18 | 18 | 0 | 0.00 | — | — | — |
| EK | 10 | 18 | 5 | 13 | 72.22 | $P < 0.001$ | n/s | — |
| EK | 100 | 13 | 5 | 13 | 72.22 | $P < 0.001$ | n/s | — |
| EK | 1000 | 18 | 1 | 17 | 94.44 | $P < 0.001$ | $P < 0.05$ | — |
| Amp | MED | 18 | 9 | 9 | 50.00 | $P < 0.05$ | — | — |
| EK + Amp | 10 | 18 | 1 | 17 | 94.44 | $P < 0.001$ | $P < 0.05$ | n/s |
| EK + Amp | 100 | 18 | 1 | 17 | 94.44 | $P < 0.001$ | $P < 0.05$ | n/s |
| EK + Amp | 1000 | 18 | 0 | 18 | 100.00 | $P < 0.001$ | $P < 0.05$ | n/s |

* n/s: not statistically significant; "Control", saline treated; "AA", ampicillin treated; "CD", comparison of EK + Amp with the corresponding dose of EK only.

TABLE 11

Survival Statistics: 36 Hours After Challenge with *S. aureus**

| Test article | Dose (mcg/kg) | Total | Deaths | Survivors | Survival (%) | Chi-square Statistics compared to: Control | AA | CD |
|---|---|---|---|---|---|---|---|---|
| Control | — | 18 | 18 | 0 | 0.00 | — | — | — |
| EK | 10 | 18 | 9 | 9 | 50.00 | P < 0.05 | n/s | — |
| EK | 100 | 18 | 9 | 9 | 50.00 | P < 0.05 | n/s/ | — |
| EK | 1000 | 18 | 4 | 14 | 77.78 | P < 0.001 | P <0.05 | — |
| Amp | MED | 18 | 18 | 5 | 27.78 | P < 0.05 | — | — |
| EK + Amp | 10 | 18 | 2 | 16 | 88.89 | P < 0.001 | P < 0.001 | P < 0.05 |
| EK + Amp | 100 | 18 | 2 | 16 | 88.89 | P < 0.001 | P < 0.001 | P < 0.05 |
| EK + Amp | 1000 | 18 | 0 | 18 | 100.00 | P < 0.001 | P < 0.001 | P < 0.05 |

* n/s: not statistically significant; "Control", saline treated; "AA", ampicillin treated; "CD", comparison of EK + Amp with the corresponding dose of EK only.

TABLE 12

Survival Statistics: 48 Hours After Challenge with *S. aureus**

| Test article | Dose (mcg/kg) | Total | Deaths | Survivors | Survival (%) | Chi-square statistics compared to: Control | AA | CD |
|---|---|---|---|---|---|---|---|---|
| Control | — | 18 | 18 | 0 | 0.00 | — | — | — |
| EK | 10 | 18 | 13 | 5 | 27.78 | P < 0.05 | n/s/ | — |
| EK | 100 | 18 | 13 | 5 | 27.78 | P < 0.05 | n/s | — |
| EK | 1000 | 18 | 10 | 8 | 44.44 | P < 0.05 | n/s | 0 |
| Amp | MED | 18 | 13 | 5 | 27.78 | P < 0.05 | — | — |
| EK + Amp | 10 | 18 | 4 | 14 | 77.78 | P < 0.001 | P < 0.05 | P < 0.05 |
| EK + Amp | 100 | 18 | 4 | 14 | 77.78 | P < 0.001 | P < 0.05 | P < 0.05 |
| EK + Amp | 1000 | 18 | 2 | 16 | 88.89 | P < 0.001 | P < 0.001 | P < 0.05 |

* n/s: not statistically significant; "Control", saline treated; "AA", ampicillin treated; "CD", comparison of EK + Amp with the corresponding dose of EK only.

TABLE 13

Survival Statistics: 72 Hours After Challenge with *S. aureus**

| Test article | Dose (mcg/kg) | Total | Deaths | Survivors | Survival (%) | Chi-square statistics compared to: Control | AA | CD |
|---|---|---|---|---|---|---|---|---|
| Control | — | 18 | 18 | 0 | 0.00 | — | — | — |
| EK | 10 | 18 | 13 | 5 | 27.78 | P < 0.05 | n/s | — |
| EK | 100 | 18 | 13 | 5 | 27.78 | P < 0.05 | n/s | — |
| EK | 1000 | 18 | 13 | 5 | 27.78 | P < 0.05 | n/s | — |
| Amp | MED | 18 | 13 | 5 | 27.78 | P < 0.05 | — | — |
| EK + Amp | 10 | 18 | 4 | 14 | 77.78 | P < 0.001 | P < 0.05 | P < 0.05 |
| EK + Amp | 100 | 18 | 4 | 14 | 77.78 | P < 0.002 | P < 0.05 | P < 0.05 |
| EK + Amp | 1000 | 18 | 2 | 16 | 88,89 | P < 0.001 | P < 0.001 | P < 0.05 |

* n/s: statistically significant; "Control", saline treated; "AA", ampicillin treated; "CD", comparison of EK + Amp with the corresponding dose of EK only.

EXAMPLE 8

Utility of HM897 In Combination Therapies for Treating Systemic Bacterial Infections Preparations of the pentapeptide peptide Thr-Ala-Glu-Glu-Lys [SEQ ID NO:2] (HM897) were tested in an animal model of antibiotic resistant bacterial infection, i.e., methicillin-resistant staphylococcal infection. In EXAMPLE 7, above, mice inoculated with lethal doses of methicillin-resistant (abbreviated "MR") *Staphylococcus aureus* were shown to have markedly enhanced survival when treated with the EK pharmaceutical preparation. The experiments were repeated, but here using the HM897 pentapeptide instead of the EK dipeptide. The results presented below show that although HM897 alone appeared to have no measurable specific anti-microbial activity (MIC values >1000) in microbiological petri culture experiments, it was effective to promote survival of animals injected with a lethal dose of staphylococci.

As in EXAMPLE 7, above, Balb/c mice were injected ip with $10 \times LD_{50}$ doses of a methicillin-resistant *S. aureus* suspended in brain-heart infusion broth containing 5 percent mucin. Different treatments were administered s.c., one hour after the bacterial challenge (i.e., a therapeutic protocol) and mortality was recorded over the next three days. Where mortality was reduced to an extent that permitted analysis (>50% survival) the minimum effective dose (MED) of HM897 was determined.

Two control groups were included in the experiment. First, HM897 was administered prior to bacterial challenge (prophylactic regimen), and saline was administered i.p.

post-challenge. The number of survivors at 72 hours was determined. Second, saline was administered prophylactically, and Ampicillin was administered i.p., at the MED, within one hour of bacterial challenge. The number of survivors was recorded at 72 hrs.

To evaluate whether therapeutic treatments with HM897 were capable of augmenting the effects of an antibiotic, HM897 treatments were administered alone, or in combination therapy with Ampicillin as follows: namely, HM897 was administered ip in a prophylactic treatment regimen on each of three successive days prior to bacterial challenge, and then within one hour after bacterial challenge Ampicillin treatment was administered. The effects of HM897 treatments were evaluated over a range of dosages: namely, 10, 100, and 1000 μg/kg. The bacterial challenge consisted of an i.p. injection of 10×LD$_{50}$ doses of S. aureus. Mortality was recorded at 12, 24, 36, 48, and 72 hours.

The study design is depicted diagrammatically in FIG. 5.

In untreated control animals bacterial challenge with 10 -LD50 doses of S. aureus resulted in visibly rapid deterioration of animals condition with the onset of acute peritonitis. Mortality in the saline treated control group was 100%. Efficacy of HM897 treatments was determined by comparisons with animals in saline-treated and ampicillin-treated control groups. The results of the experiment are summarized in TABLES 14–18 below. HM897 treatments reduced mortality. Mortality for animals in the saline-treated control group was 94% at 24 hours, and 0% at 36 hours. In contrast, mortality was only 39% in certain of the HM897-treated groups at 36 hours. The effect of co-administration of Ampicillin resulted in 77% to 94% survival at 36 hours compared to only 28% survival in the group receiving ampicillin alone. By 72 hours 22–39% of the animals receiving only HM897 were alive, and 72–94% survived in the groups treated with both Ampicillin and HM897.

Figure 6:
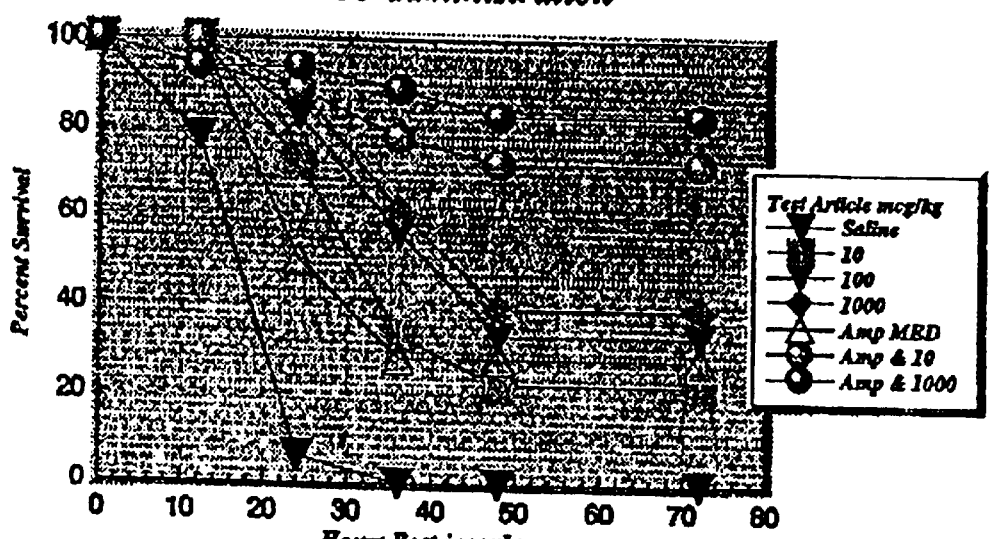
FIG. 6 illustrates survival of bacterially-infected mice treated with HM897 with and without adjuvant antibiotics.
Figure 7:
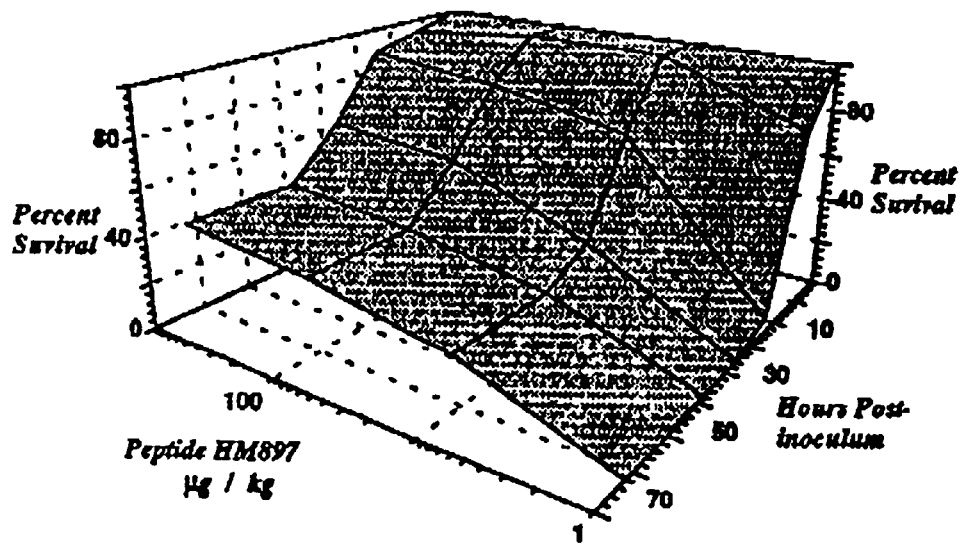
FIG. 7 illustrates survival of bacterially-infected mice treated with HM897 with adjuvant antibiotics.
Figure 8:
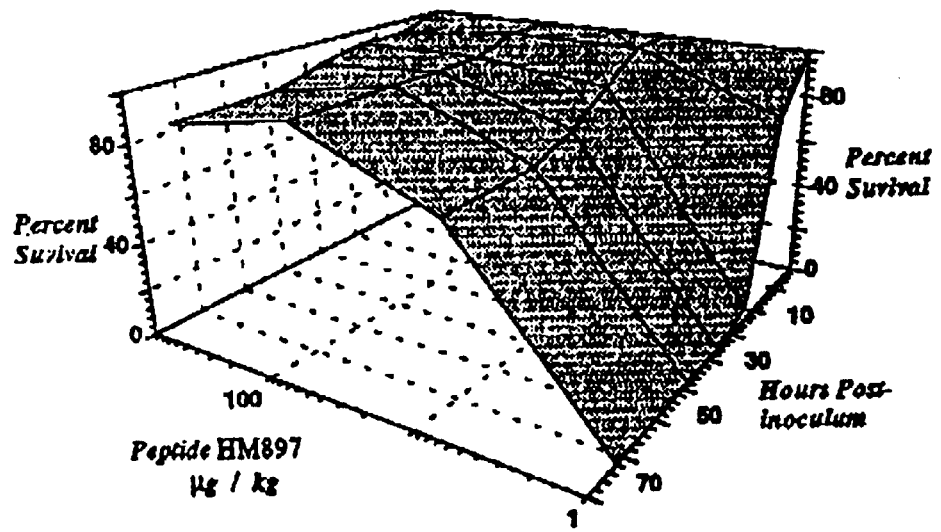
FIG. 8 illustrates survival of bacterially-infected mice treated with HM897 without adjuvant antibiotics.

The results indicate that mice treated prophylactically with HM897 were afforded protection to a subsequent bacterial challenge, i.e., mortality in the HM897 pre-treated groups of animals was dramatically lower than in non-treated or saline-treated controls. Moreover, compared with Ampicillin or HM897 alone, mortality was reduced 2-fold in groups of mice pre-treated with HM897, challenged with bacteria, and then treated with Ampicillin. FIGS. 6–8 graphically depict the results obtained in the groups of animals receiving the combination therapy. The results demonstrate a synergistic effect between HM897 treatments and antibiotic therapy.

TABLE 14

Survival Statistics: 12 Hours After Challenge with S aureus*

| Test article | Dose (mcg/kg) | Total | Deaths | Survivors | Survival (%) | Chi-square statistics compared to: Control | AA | CD |
|---|---|---|---|---|---|---|---|---|
| Control | — | 18 | 4 | 14 | 77.78 | — | — | — |
| HM897 | 10 | 18 | 0 | 18 | 100.00 | P < 0.05 | n/s | — |
| HM897 | 100 | 18 | 0 | 18 | 100.00 | P < 0.05 | n/s | — |
| HM897 | 1000 | 18 | 1 | 17 | 94.44 | n/s | n/s | — |
| Amp | MED | 18 | 0 | 18 | 100.00 | P < 0.05 | — | — |
| HM897 + Amp | 10 | 18 | 0 | 18 | 100.00 | P < 0.05 | n/s | n/s |
| HM897 + Amp | 100 | 18 | 0 | 18 | 100.00 | P < 0.05 | n/s | n/s |
| HM897 + Amp | 1000 | 18 | 1 | 178 | 94.44 | n/s | n/s | n/s |

* n/s: not statistically significant; "Control", saline treated; "AA", ampicillin treated; "CD", comparison of HM897 + Amp with the corresponding dose of HM897 only

TABLE 15

Survival Statistics: 24 Hours After Challenge with S. aureus*

| Test article | Dose (mcg/kg) | Total | Deaths | Survivors | Survival (%) | Chi-square statistics compared to: Control | AA | CD |
|---|---|---|---|---|---|---|---|---|
| Control | — | 18 | 17 | 1 | 5.56 | — | — | — |
| HM897 | 10 | 18 | 5 | 13 | 72.22 | P < 0.001 | n/s | — |
| HM897 | 100 | 18 | 3 | 15 | 83.33 | P < 0.001 | P < 0.05 | — |
| HM897 | 1000 | 18 | 2 | 16 | 88,89 | P < 0.001 | P < 0.05 | — |
| Amp | MED | 18 | 9 | 9 | 50.00 | P < 0.05 | — | — |
| HM897 + Amp | 10 | 18 | 2 | 16 | 88.89 | P < 0.001 | P < 0.05 | n/s |
| HM897 + Amp | 100 | 18 | 1 | 17 | 94.44 | P < 0.001 | P < 0.05 | n/s |
| HM897 + Amp | 1000 | 18 | 1 | 17 | 94.44 | P < 0.001 | P < 0.05 | n/s |

* n/s: not statistically significant; "Control", saline treated; "AA", ampicillin treated; "CD", comparison of HM897 + Amp with the corresponding dose of HM897 only.

TABLE 16

Survival Statistics: 36 Hours After Challenge with *S. aureus**

| Test article | Dose (mcg/kg) | Total | Deaths | Survivors | Survival (%) | Chi-square statistics compared to: Control | AA | CD |
|---|---|---|---|---|---|---|---|---|
| Control | — | 18 | 18 | 0 | 0.00 | — | — | — |
| HM897 | 10 | 18 | 12 | 6 | 33.33 | P < 0.001 | n/s | — |
| HM897 | 100 | 18 | 8 | 10 | 55.56 | P < 0.001 | n/s | — |
| HM897 | 1000 | 18 | 7 | 11 | 61.11 | P < 0.001 | P < 0.05 | — |
| Amp | MED | 18 | 13 | 5 | 27.78 | P < 0.05 | — | — |
| HM897 + Amp | 10 | 18 | 4 | 14 | 77.78 | P < 0.001 | P < 0.05 | P < 0.05 |
| HM897 + Amp | 100 | 18 | 1 | 17 | 94.44 | P < 0.001 | P < 0.001 | P < 0.05 |
| HM897 + Amp | 1000 | 18 | 2 | 16 | 88.89 | P < 0.001 | P < 0.001 | n/s |

* n/s: not statistically significant; "Control", saline treated; "AA", ampicillin treated; "CD", comparison of HM897 + Amp with the corresponding dose of HM897 only.

TABLE 17

Survival Statistics: 48 Hours After Challenge with *S. aureus**

| Test article | Dose (mcg/kg) | Total | Deaths | Survivors | Survival (%) | Chi-square statistics compared to: Control | AA | CD |
|---|---|---|---|---|---|---|---|---|
| Control | — | 18 | 18 | 0 | 0.00 | — | — | — |
| HM897 | 10 | 18 | 14 | 4 | 22.22 | P < 0.05 | n/s | — |
| HM897 | 100 | 18 | 12 | 6 | 33.33 | P < 0.05 | n/s | — |
| HM897 | 1000 | 18 | 11 | 7 | 38.89 | P < 0.05 | n/s | — |
| Amp | MED | 18 | 13 | 5 | 27.78 | P < 0.05 | — | — |
| HM897 + Amp | 10 | 18 | 5 | 13 | 72.22 | P < 0.001 | P < 0.05 | P < 0.05 |
| HM897 + Amp | 100 | 18 | 1 | 17 | 94.44 | P < 0.001 | P < 0.001 | P < 0.001 |
| HM897 + Amp | 1000 | 18 | 3 | 15 | 83.33 | P < 0.001 | P < 0.05 | P < 0.05 |

* n/s: not statistically significant; "Control", saline treated; "AA", ampicillin treated; "CD", comparison of HM897 + Amp with the corresponding dose of HM897 only.

TABLE 18

Survival Statistics: 72 Hours After Challenge with *S. aureus**

| Test article | Dose (mcg/kg) | Total | Deaths | Survivors | Survival (%) | Chi-square statistics compared to: Control | AA | CD |
|---|---|---|---|---|---|---|---|---|
| Control | — | 18 | 18 | 0 | 0.00 | — | — | — |
| HM897 | 10 | 18 | 14 | 4 | 22.22 | P < 0.05 | n/s | — |
| HM897 | 100 | 18 | 12 | 6 | 33.33 | P < 0.05 | n/s | — |
| HM897 | 1000 | 18 | 11 | 7 | 38.89 | P < 0.05 | n/s | — |
| Amp | MED | 18 | 13 | 5 | 27.78 | P < 0.05 | — | — |
| HM897 + Amp | 10 | 18 | 5 | 13 | 72.22 | P < 0.001 | P < 0.05 | P < 0.05 |
| HM897 + Amp | 100 | 18 | 1 | 17 | 94.44 | P < 0.001 | P < 0.001 | P < 0.001 |
| HM897 + Amp | 1000 | 18 | 3 | 15 | 83.33 | P < 0.001 | P < 0.05 | P < 0.05 |

* n/s: not statistically significant; "Control", saline treated; "AA", ampicillin treated; "CD", comparison of HM897 + Amp with the corresponding dose of HM897 only.

EXAMPLE 9

Use of HM897 of Augmenting Protection Afforded by Vaccination

This example demonstrates the augmentation of a vaccine by administration of a peptide Thr-Ala-Glu-Glu-Lys [SEQ ID NO:2] (HM897). Administration of HM897 following vaccination provided enhanced protection against infection.

Background of the Animal Model System:

Since the following investigational animal model system may not be known to all pharmaceutical immunologists, the following background information is provided.

The following studies were performed in hatchling fish, i.e., rainbow trout (*Oncorhynchus mykiss*). In these animals, the lymphoid system is poorly developed, with demonstrable immune incompetence. The animal model has the advantage that pharmacologic agents added to the tank water are rapidly and completely absorbed across the gills into the systemic circulation of the animals. Contact with formed preformed blood elements (i.e., leukocytes) is also favored, since greater than 80% of total blood volume at any time may be present in the gills. These animals also exhibit features common to mammalian immune systems, e.g., hatchlings exposed to certain antigens prior to maturation, instead of responding by producing antibodies, develop 'tolerance' (i.e., subsequent immune responses are blocked). The effects of tolerance/blocking may last for several weeks, or, in more mature fish the loss maybe permanent leaving the animals highly to future infection. Mediators of innate immunity have also been reported in fish ova, including C-reactive protein-like precipitins, and lecithin-like agglutinins. In addition, reports suggest that in certain fishes maternal antibodies may be passively transferred to offspring through the yolk salk proteins. However, passive transfer of immunity has not been observed in salmonids. The major lymphoid organs in teleost fish are the thymus, kidney, and spleen. The thymus is composed of developing lymphocytes, and as in other vertebrates, it is as the reservoir of naive lymphocytes that subsequently differentiate and become committed to form peripheral T-cells that reside in peripheral blood and lymphoid organs. In hatchling development, lymphocytes first develop in the thymus, and in rainbow trout the fully differentiated thymus is separated from the external environment only by a single layer of epithelial cells. That latter cells possess cell membrane pores that are up to 20 Å in diameter in electron micrographs. Epithelial fenestrations in the thymic rudiment are observed to close during maturation of the fish.

Peripheral lymphoid cells appear in the blood and lymphoid organs of the trout within 3 days of hatching. The rate of growth of the lymphoid tissues exceeds the rest of the body's rate during the first few weeks of life. The ratio of the weight of the lymphoid organs to body weight reaches a peak at 2 months of age, i.e., when the trout are normally about 0.5 grams. An intense period of mitotic activity occurs within the thymus during these first few months. Thymic involution appears to occur after approximately 9 months.

Morphologically identifiable lymphocytes are seen in early hatchlings, and the T- and B-lymphocytes develop at different speeds. The majority of cells have no surface immunoglobulins prior to 48 days, and the ability to produce antibody prior to this age is inconsistent. The latter observations suggest that B-cells and T-suppressor-cells may become functionally active at about 4 weeks of age, and that T-helper cells only mature at about 8 weeks of age. In these varied respects, development of the fish immune system is similar to that in rodents except that self-marking (i.e., developing tolerance to self-antigens) may take longer in fish than in mice.

This animal model has the advantage that relatively large numbers of animals can be used in an experiment (e.g., 50) under very uniform conditions of treatment and at relatively low cost.

Vaccine Animal Model: Study Design:

In the present investigation, fish were inoculated ip at approximately 12 weeks of age with vaccine antigens. A course of HM897 treatments was administered either before vaccination, or after vaccination. The amount of HM897 used in the treatments was varied.

The study was conducted using Rainbow trout and a direct comparison was made of the protection afforded by a standard fish vaccine administered alone, or in combination with an HM897 treatment course consisting of daily exposure to varying dosages of HM897. Vaccine immunity was evaluated at 7 days (post vaccination) by challenging the fish ip with Vibrio anguillarum (V-775), an aquatic bacteria that causes fatal vibriosis, typically within 3–5 days after exposure.

Hatchling fish weighing approximately 5 grams were used as test organisms. The fish were maintained in a consistent water quality having an aerated flow-through system with a flow rate of approximately 30 liters per hour. The fish were not fed 48 hours prior to testing.

Determination of $LD_{75}$ for Bacterial Challenge:

The $LD_{25}$–$LD_{100}$ dosage level of the challenge bacteria Vibrio anquillarum (V-775) was determined by injecting fish in different groups (15/group) ip with 0.1 mL of different dilutions of a uniform bacterial culture. For these studies the challenge bacteria were grown for 48 hours at 25° C. in trypticase soy broth to a standard optical density, and then diluted in 0.9% saline for inoculation. Fish mortality was used as the endpoint, and deaths were recorded daily. The $LD_{75}$ dilution of V. anguillarum (i.e., the dilution calculated to give 75% mortality in non-vaccinated fish) was determined to be in the range of $10^{-4}$ to $10^{-5}$. The results are presented in TABLE 19, below, as daily cumulative mortality values. The results of this experiment established the LD75 of the challenge bacterial. Each group of fifteen fish were challenged with bacterial dilution of $10^{-2}$, $10^{-3}$, $10^{-4}$, or $10^{-5}$. Nine days after injection of the bacterial dilutions the accumulated mortalities were as follows: namely, at $10^{-2}$ bacterial dilution 14 fish were dead (93.3% mortality); at $10^{-3}$ bacterial dilution 13 fish were dead (86.7% mortality); at $10^{-4}$ bacterial dilution 10 fish were dead (66.7% mortality); and, at $10^{-5}$ bacterial dilution 10 fish were dead (66.7% mortality).

TABLE 19

Cumulative Mortality for Rainbow Trout
Inoculated with Vibrio anguillarum: $LD_{75}$ Determination

| Group | Dilution | Number of Fish | 06/30 | 07/01 | 07/02 | 07/03 | 07/04 | 07/05 | 07/06 | 07/07 | 07/08 | 07/09 |
|---|---|---|---|---|---|---|---|---|---|---|---|---|
| 1 | $10^{-2}$ | 15 | 0 | 0 | 14 | 14 | 14 | 14 | 14 | 14 | 14 | 14 |
| 2 | $10^{-3}$ | 15 | 0 | 0 | 6 | 9 | 13 | 13 | 13 | 13 | 13 | 13 |
| 3 | $10^{-4}$ | 15 | 0 | 0 | 0 | 5 | 9 | 10 | 10 | 10 | 10 | 10 |
| 4 | $10^{-5}$ | 15 | 0 | 0 | 0 | 4 | 7 | 10 | 10 | 10 | 10 | 10 |

An $LD_{75}$ dose of V. anguillarum was determined in these experiments to be a $10^{-4}$ to $10^{-5}$ dilution of a log-phase culture of a standardized optical density.

Experimental Protocol:

Fish were divided into 21 groups consisting of 50 fish per group. Each group of 50 fish was maintained in two 10 gallon tanks (25 fish/tank). HM897 treatment consisted of immersing the fish daily for a period of 5 minutes each day, on each of 7 consecutive days, in a 38 L tank containing a particular test concentration of HM897. In the latter case, HM897 (as a powder) was added to different 38 L tanks of water immediately prior to adding the test fish in the following amounts: namely, 2.5 µg/38 L, 10 µg/38 L, 25 µg/38 L, 50 µg/38 L, 75 µg/38 L, 100 µg/38 L, 150 µg/38 L, and 250 µg/38 L. At the conclusion of the 7 day HM897 treatment challenge with V. anguillarum bacterium consisted of ip injection of 0.1 mL of an $LD_{75}$ dilution of log-phase bacteria.

To evaluate possible effects of HM897 on development of immunity, HM897 treatments were administered before and after vaccination with a standard fish vaccine antigen mixture made from V. anguillarum (V-775). The vaccine was made using a standard fermentation and extraction process according to standard aquaculture industry standards for vibrio vaccines. Vaccination consisted of ip injection of 0.1 mL of vaccine antigens.

The fish were observed daily for mortality.

The experimental groups were as follows: namely,

Group I (normal control) consisted of 50 unvaccinated fish who were observed for three weeks. These fish did not receive treatment with HM897 and were not challenged with bacteria. They served as a control for the aquaculture conditions.

Group II (unvaccinated untreated control) consisted of 50 unvaccinated fish challenged with $10^{-4}$ dilution of Vibrio anguillarum (V-775) and observed for mortality.

Group III (vaccinated challenged) consisted of 50 fish who were vaccinated on day 1 and then challenged with to $10^{-4}$ dilution of Vibrio anguillarum (V-775). The fish were not treated with HM897.

Group IVa (vaccinated then HM897-treated) consisted of 50 fish who were vaccinated and then subsequently treated with HM897 on each of 7 consecutive days (as above). In this group the final HM897 concentration in the tank was 2.5 µg/38 L (0.07 pg/ml). On day 7, after the final HM897 treatment, the fish were challenged with the $10^{-4}$ dilution of V. anguillarum (V-775) and mortality was recorded over the next several days. Animals in Group IVb, like Group IVa (above) were treated daily for 7 days with HM897, but at a dose of 10 µg/38 L (0.260 pg/ml). On day 7, after the last HM897 treatment the fish were exposed to $10^{-4}$ dilution of Vibrio anguillarum (V-775) and mortality was recorded thereafter. Animals in Group IVc were treated in a manner identical to those in Groups IVa and IVb, above, but treatments with HM897 were at a dose of 50 µg/38 L (1.3 pg/mL) of HM897. Group IVd, was treated in the same manner as Groups IVa–c, above, but HM897 treatments were at a dose of 100 µg/38 L (2.6 pg/mL) of HM897.

Group Va (unvaccinated-HM897 treated) consisted of 50 fish treated on each of 7 consecutive days for 5 minutes each with 10 µg/38 L (0.26 pg/mL) of HM897. On day 7, after the last HM897 treatment, the fish challenged with the $10^{-4}$ dilution of Vibrio anguillarum (V-775) and mortality was recorded thereafter. Group Vb consisted of 50 fish treated in a manner identical to those in Group Va, above, but with 25 µg/38 L (0.7 pg/mL) of HM897. Group Vc was constituted and treated in a manner identical to Group Va, but treatments were with 75 µg/38 L (2 pg/mL) of HM897. Group Vd was constituted and treated in a manner identical to Group Va, but treatments were with 150 µg/38 L (3.9 pg/mL) of HM897. Group Ve was constituted and treated in a manner identical to Group Va, but treatments were with 250 µg/38 L (6.5 pg/mL) of HM897.

All of the groups were observed for a period of twenty-one days, and the effect of the efficacy of the HM897 and/or vaccination treatments were evaluated based mortaly. The design of this study is summarized in TABLE 20, below.

TABLE 20

Summary of Experimental Design for HM897 and Retromedine ™: Immunologic Studies in Rainbow Trout*

| Group | Vaccinated Day 1 | Test Article | Test Article µg/38 liters Day 1 | Inoculated LD75 Day 7 | Number of Fish |
|---|---|---|---|---|---|
| I | no | none | none | no | 50 |
| II | no | none | none | yes | 50 |
| III | yes | none | none | yes | 50 |
| IVa | yes | HM897 | 2.5 | yes | 50 |
| IVb | yes | HM897 | 10 | yes | 50 |
| IVc | yes | HM897 | 50 | 5yes | 50 |
| IVd | yes | HM897 | 100 | yes | 50 |
| Va | no | HM897 | 10 | yes | 50 |
| Vb | no | HM897 | 25 | yes | 50 |
| Vc | no | HM897 | 75 | yes | 50 |
| Vd | no | HM897 | 150 | yes | 50 |
| Ve | no | HM897 | 250 | yes | 50 |

Vaccine Augmentation Study: Results:

The daily accumulated mortalities are shown in TABLE 21. The number of the mortalities for each group were as follows: namely, in Group I (normal control) there was no mortality; in Group II (unvaccinated untreated control) 31 of the 50 fish died from bacterial infection (62% mortality); in Group III (vaccinated challenged) 15 fish died from bacterial infection (30% mortality); in Group IVa (vaccinated HM897-treated challenged) 13 fish died from bacterial infection (26% mortality); in Group IVb (vaccinated HM897-treated challenged) 7 fish died from bacterial infection (14% mortality); in Group IVc (vaccinated HM897-treated challenged) 10 fish died from bacterial infection (20% mortality); in Group IVd (vaccinated HM897-treated challenged) 17 fish died from bacterial infection (34% mortality); in Group Va (HM897-treated vaccinated challenged) 33 fish died from bacterial infection (66% mortality); in Group Vb (HM897-treated vaccinated challenged) 33 fish died from bacterial infection (66% mortality); in Group Vc (HM897-treated vaccinated challenged) 34 fish died from bacterial infection (68% mortality); in Group Vd (HM897-treated vaccinated challenged) 32 fish died from bacterial infection (64% mortality); and, in Group Ve (HM897-treated vaccinated challenged) 34 fish died from bacterial infection (68% mortality). The results are presented in TABLE 21, below.

TABLE 21

Summary of Cumulative (Cum.) Mortality for HM897 Treated Rainbow Trout Infected with *Vibrio anguillarum*

| Day Group | 1 | 2.10 | 11 | 12 | 13 | 14 | 15 | 16 | 17 | 18 | 19 | 20 | 21 | Total Cum. Mortality |
|---|---|---|---|---|---|---|---|---|---|---|---|---|---|---|
| I   | 0 | 0 | 0 | 0 | 0  | 0  | 0  | 0  | 0  | 0  | 0  | 0  | 0  | 0 |
| II  | 0 | 0 | 0 | 0 | 22 | 27 | 29 | 31 | 31 | 31 | 31 | 31 | 31 | 31 |
| III | 0 | 0 | 0 | 0 | 8  | 14 | 14 | 15 | 15 | 15 | 15 | 15 | 15 | 15 |
| IVa | 0 | 0 | 0 | 0 | 1  | 7  | 10 | 13 | 13 | 13 | 13 | 13 | 13 | 13 |
| IVb | 0 | 0 | 0 | 0 | 1  | 5  | 6  | 6  | 7  | 7  | 7  | 7  | 7  | 7 |
| IVc | 0 | 0 | 0 | 0 | 1  | 5  | 10 | 10 | 10 | 10 | 10 | 10 | 10 | 10 |
| IVd | 0 | 0 | 0 | 0 | 8  | 15 | 16 | 17 | 17 | 17 | 17 | 17 | 17 | 17 |
| Va  | 0 | 0 | 0 | 0 | 16 | 24 | 28 | 33 | 33 | 33 | 33 | 33 | 33 | 33 |
| Vb  | 0 | 0 | 0 | 0 | 16 | 25 | 32 | 33 | 33 | 33 | 33 | 33 | 33 | 33 |
| Vc  | 0 | 0 | 1 | 1 | 21 | 29 | 32 | 33 | 34 | 34 | 34 | 34 | 34 | 34 |
| Vd  | 0 | 0 | 0 | 0 | 14 | 23 | 28 | 32 | 32 | 32 | 32 | 32 | 32 | 32 |
| Ve  | 0 | 0 | 0 | 0 | 14 | 25 | 30 | 32 | 34 | 34 | 34 | 34 | 34 | 34 |

TABLE 22

Summary of Results: Trout Mortality Data

| Group | Vaccinated Day 1 | Test Article | Test Article µg/38 liters Day 1 | Inoculated LD75 Day 7 | Total Cum. Mortality | Percent Mortality |
|---|---|---|---|---|---|---|
| I    | no  | none    | none | no  | 0  | 0 |
| II   | no  | none    | none | yes | 31 | 62 |
| III  | yes | vaccine | none | yes | 15 | 30 |
| IVa  | yes | HM897   | 2.5  | yes | 13 | 26 |
| IVb  | yes | HM897   | 10   | yes | 7  | 14 |
| IVc  | yes | HM897   | 50   | yes | 10 | 20 |
| IVd  | yes | HM897   | 100  | yes | 17 | 34 |
| Va   | no  | HM897   | 10   | yes | 33 | 66 |
| Vb   | no  | HM897   | 25   | yes | 33 | 66 |
| Vc   | no  | HM897   | 75   | yes | 34 | 68 |
| Vd   | no  | HM897   | 150  | yes | 32 | 64 |
| Ve   | no  | HM897   | 250  | yes | 34 | 68 |

A typical commercial vaccine usually affords only 60% to 70% protection to a population of vaccinated fish. The vaccinated group (Group III) showed 30% mortality, i.e., vaccination afforded 70% protection against the challenge bacteria in this animal model system.

Figure 9:
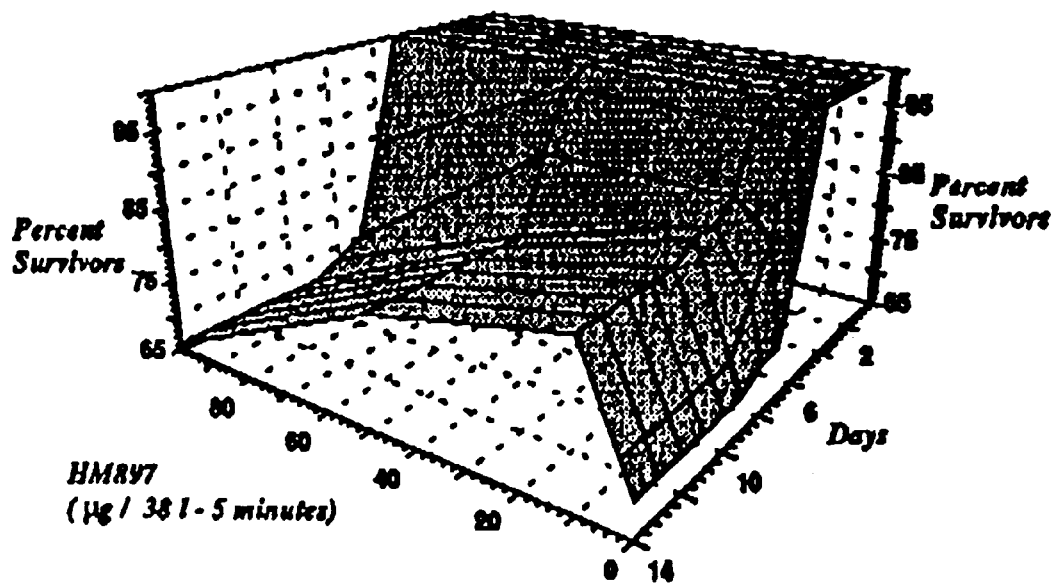
FIG. 9 illustrates survival of vaccinated fish treated with different amounts of HM897.

The fish in groups IVa, IVb, IVc, and IVd were vaccinated and then each exposed to a different concentrations of HM897 for 5 minutes on a daily treatment regimen. Each group revealed a different level of protection against the challenge bacteria. In Group IVb with 10 µg of HM897 in 38 liters for 5 minutes inoculated with challenge *Vibrio anguillarum* 7 days after vaccination had the lowest mortalities at 14% compared to the group receiving vaccine alone at 30% (FIG. 9).

Figure 10:
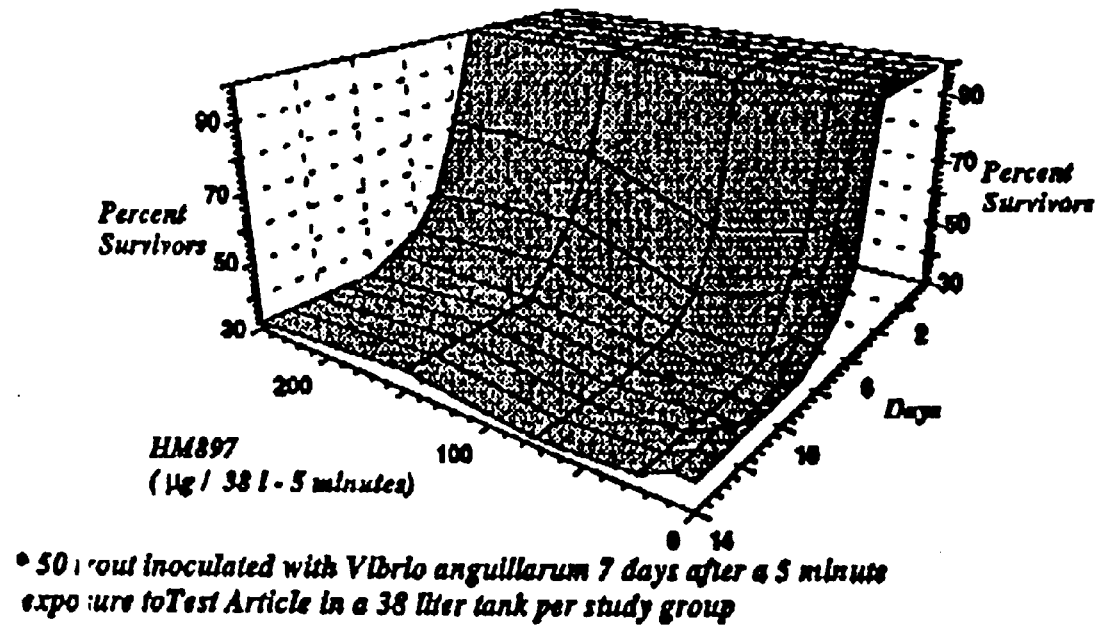
FIG. 10 illustrates survival of unvaccinated fish treated with different amounts of HM897.

The groups treated with different levels of HM897 exposure without vaccine (Groups Va to Ve) showed no protection against the bacterial infection (TABLE 21, FIG. 10). The percentage of the fish mortalities in these groups were similar to the control group (Group II) in which no treatment was provided excepting challenge with *Vibrio anguillarum*. These findings indicate that HM897 has a statistically significant effect in augmenting the protection afforded by vaccination.

EXAMPLE 10

Effects of HM897 on T-lymphocytes in "Nude" Mice

Homozygous nude mice (i.e., nu/nu) are genetically deficient in a thymus and exhibit an immunodeficiency in T-lymphocyte functions, e.g., cell mediated immunity and humoral immune responses to T-dependent antigens. Heterozygous nude mice (i.e., nu$^+$/nu) are immunocompetent and serve as effective positive controls in evaluating different aspects of nu/nu unresponsiveness. Nu/nu immune deficiency results from the requirement of T-lymphocytes during their differentiation process for thymic humoral factors.

In the course of a humoral immune response antibody production switches from synthesis of IgM to synthesis of IgG between day 3 and 7 of the response. Mature T-lymphocytes are required to effect the switch from IgM to IgG.

Sheep erythrocytes ($E_s$) express both T-dependent and T-independent antigens. Levels of serum antibodies to $E_s$ are conveniently measured by titrating hemagglutination, i.e., antibody-mediated crosslinking of $E_s$ (heagglutination titer, abbreviated HA). IgM antibodies can be distinguished from IgG antibodies by virtue of their sensitivity to reducing agents, i.e., 2-mercaptoethanol (2-ME). A decrease in hemagglutination titer following treatment of serum with 2-ME is thus indicative of the presence of IgM, while no decrease is indicative of IgG.

To evaluate whether HM897 could effect the function of immature T-lymphocytes in nu/nu mice, experiments were conducted in which animals were pretreated on each of 2 consecutive days with 10 µg/kg HM897, then immunized (ip) with $E_s$, and then treated daily for an additional 2 days with 10 µg/kg HM897. Hemagglutination titers and 2-ME sensitivity of the titers served to measure production of serum IgM and IgG antibodies in circulation 12 days after the injection of the $E_s$. The results presented in TABLE 23 show a dramatic >90% increase in the levels of IgM serum antibodies (i.e., 3-ln(2)). The sensitivity of the assay did not permit a determination of whether HM897 stimulated an isotypic switch from IgM to IgG.

TABLE 23

HM897 Treatments Increase Serum Antibody Titer-In(2) and IgM Antibodies in Nude Mice Immunized with Sheep Erythrocytes

| Genotype | Group No. | Treatment | Immunization | Serum HA Titer (Total Ig) | Titer after 2-ME (IgG) | Difference (IgM)* |
|---|---|---|---|---|---|---|
| nu+/nu | 1 | Saline | – | <3† | <4† | 0 |
| nu+/nu | 2 | Saline | + | 9.7 ± 0.5 | 7.5 ± 0.5 | 2.2 |
| nu/nu | 3 | Saline | + | <4† | <4.8† | 0 |
| nu/nu | 4 | HM897 | + | 4.8 ± 0.4 | 7.0 ± 1.3 | >3 |

*IgM determined by difference, i.e., (Total Ig Titer - IgG) = IgM titer; In(2) titer, serial dilution endpoint HA titer; †, assay variability did not allow an accurate determination of titer at less than a 1/16 dilution (e.g., mouse blood group heterophile antibodies titers can be 1/8–1/16).

EXAMPLE 11

Effects of HM897 on Retroviral Infection

Rauscher murine leukemia (Ra MuLV) virus induces erythroleukemia in Balb/c mice that is progressive with splenomegaly within the first 21 days of infection and death usually within 50 days. Correlates of infection that may be useful in monitoring include increases in spleen weight, anti-viral antibody titers in serum, or reverse transcriptase activity in lymphoid cells.

For the present study, Balb/c mice (6 mice/group) were treated prophylactically on each of 5 successive days by ip injection (0.2 ml) of either: (Group 1) saline (normal control), (Group 2) saline (negative control), (Group 3) 0.1 mcg/kg HM897, (Group 4) 1 mcg/kg HM897, (Group 5) 10 mcg/kg HM897 or (Group 6) 50 mcg/kg HM897. On day 6 the animals in Groups 2–6 were inoculated ip with 0.1 ml of Ra MuLV. All animals were sacrificed on day 26 (21 days after virus inoculation) and spleen weights determined. The results are presented in TABLE 24.

TABLE 24

Summary of Results: Rauscher MuLV Model

| Group | Treatment | Dose (mcg/kg) | Virus Inoculation | Mean Spleen Weight (gm) ± S.D. | Inhibition of Splenomegaly (%) ± S.D.* |
|---|---|---|---|---|---|
| 1 | None | 0 | None | 0.09 ± 0.01 | — |
| 2 | None | 0 | + | 2.39 ± 1.22 | 0 |
| 3 | HM897 | 0.1 | + | 1.63 ± 1.54 | 33 |
| 4 | HM897 | 1 | + | 1.94 ± 0.79 | 20 |
| 5 | HM897 | 10 | + | 1.64 ± 0.92 | 33 |
| 6 | HM897 | 50 | + | 0.10 ± 0.04 | 100 |

*Percent Inhibition = [(Group 2-Group 1)-(Exptl. Group-Group 1)]/(Group 2-Group 1) × 100%

EXAMPLE 12

Anti-inflammatory Activity of HM897

Anti-inflammatory activity of HM897 was evaluated in outbred rats (both sexes, 140–170 g) using an agar-induced sterile inflammatory model, mediated by histamine and serotonin (Zaks, A. S. and Suslina, M. L., 1975), wherein subplantar injection of a 0.1% agar solution into the hind foot pad of rats induces swelling (i.e., erythema and edema) that is easily measurable at about 3–5 hours, and is maintained over about 24–48 hours. The swelling is measurable using a micrometer. For the present studies foot pad swelling was recorded in outbred rats at 3–5 hr. intervals thoughout the course of the inflammation. HM897 treatment (1 µg/kg) was administered sc one hour prior to induction of inflammation. The HM897 treatment inhibited the subsequent development of foot pad swelling by 41% (as measured at 3 hours), but at later time points (i.e., days 2–5) their was no measurable anti-inflammatory effect. Following rechallenge with agar (i.e., on day 5) the HM897 treatment reduced foot pad swelling at 48 hrs. (i.e., day 7) by 23% ($p<0.01$).

All publications, patents and patent applications mentioned in this specification are herein incorporated by reference into the specification to the same extent as if each individual publication, patent or patent application was specifically and individually indicated to be incorporated herein by reference.

Although the foregoing invention has been described in some detail by way of illustration and example for purposes of clarity of understanding, it will be obvious that certain changes and modifications may be practiced within the scope of the appended claims.

---

We claim:

1. An isolated peptide of the formula R'-Glx-Glx-Lys-R" or a pharmaceutically acceptable salt thereof wherein R' is H- or a first amino acid sequence selected from Thr-Pro-, Thr-Ala-, Ser-Ala-, Ser-Pro-, Ser-Ser- and Leu-Thr-Ala-, Glx is Glu or Gln; R" is -H or a second amino acid sequence selected from -Ala, -Ala-Ala or -Ala-Val; wherein the peptide has a sequence of at least 5 amino acids; and the peptide is not Thr-Ala-Glx-Glx-Lys.

2. The peptide of claim 1 wherein the amino acids are L-amino acids.

3. The peptide of claim 2 wherein R" is -H.

4. The peptide of claim 2 which is Thr-Pro-Glu-Glu-Lys [SEQ ID NO:1].

5. The peptide of claim 2 which is Thr-Pro-Gln-Gln-Lys [SEQ ID NO:9].

6. The peptide of claim 2 which is Leu-Thr-Ala-Glx-Glx-Lys-Ala.

7. The peptide of claim 2 which is Leu-Thr-Ala-Glx-Glx-Lys-Ala-Ala.

8. The peptide of claim 2 which is Leu-Thr-Ala-Glx-Glx-Lys-Ala-Val.

9. The peptide of claim 3 wherein R' is Thr-Pro-.

10. The peptide of any one of claims 6–8 wherein Glx is Glu.

11. A pharmaceutical composition comprising a pharmaceutically acceptable carrier and an isolated peptide of the formula R'-Glx-Glx-Lys-R" or a pharmaceutically acceptable salt thereof wherein R' is H- or a first amino acid sequence selected from Thr-Pro-, Thr-Ala-, Ser-Ala-, Ser-Pro-, Ser-Ser- and Leu-Thr-Ala-, Glx is Glu or Gln; R" is -H or a second amino acid sequence selected from -Ala, -Ala-Ala or -Ala-Val; wherein the peptide has a sequence of at least 5 amino acids; and the peptide is not Thr-Ala-Glx-Glx-Lys, in an amount of 0.001% to 20% by weight.

12. The pharmaceutical composition of claim 11 wherein the amino acids are L-amino acids.

13. The pharmaceutical composition of claim 12 wherein R" is -H.

14. The pharmaceutical composition of claim 12 wherein the peptide is Thr-Pro-Glx-Glx-Lys [SEQ ID NO:14].

15. The pharmaceutical composition of claim 12 wherein the peptide is Thr-Pro-Glu-Glu-Lys [SEQ ID NO:1].

16. The pharmaceutical composition of claim 12 wherein the peptide is Thr-Pro-Gln-Gln-Lys [SEQ ID NO:9].

17. The pharmaceutical composition of claim 13 wherein R' is Thr-Pro-.

18. The pharmaceutical composition of claim 14 comprising the peptide in an amount of 0.001% to 0.01% by weight.

19. The pharmaceutical composition of claim 14 wherein the pharmaceutically acceptable carrier is an aqueous solution.

20. The pharmaceutical composition of claim 14 wherein the pharmaceutically acceptable carrier comprises a buffer selected from sodium acetate, sodium lactate, sodium chloride, potassium chloride and calcium chloride.

21. The pharmaceutical composition of claim 14 formulated as a tablet, capsule or suppository.

22. The pharmaceutical composition of claim 19 wherein the aqueous solution comprises albumin, lipoprotein or globulin.

23. The pharmaceutical composition of claim 21 further comprising an excipient, vehicle or filler.

24. The pharmaceutical composition of claim 23 comprising 0.1 mg of the peptide.

25. An isolated peptide of the formula Thr-Ala-Glx-Glx-Lys [SEQ ID NO:6] or a pharmaceutically acceptable salt thereof wherein Glx is Glu or Gln.

26. The peptide of claim 25 wherein the amino acids are L-amino acids.

27. The peptide of claim 26 which is Thr-Ala-Glu-Glu-Lys [SEQ ID NO:2].

28. The peptide of claim 26 which is Thr-Ala-Gln-Gln-Lys [SEQ ID NO:15].

29. A pharmaceutical composition comprising a pharmaceutically acceptable carrier and an isolated peptide of the formula Thr-Ala-Glx-Glx-Lys [SEQ ID NO:6] or a pharmaceutically acceptable salt thereof wherein Glx is Glu or Gln, in an amount of 0.001% to 20% by weight.

30. The pharmaceutical composition of claim 29 wherein the amino acids are L-amino acids.

31. The pharmaceutical composition of claim 30 wherein the peptide is Thr-Ala-Glu-Glu-Lys [SEQ ID NO:2].

32. The pharmaceutical composition of claim 30 wherein the peptide is Thr-Ala-Gln-Gln-Lys [SEQ ID NO:15].

33. The pharmaceutical composition of claim 30 comprising the peptide in an amount of 0.001% to 0.01% by weight.

34. The pharmaceutical composition of claim 30 wherein the pharmaceutically acceptable carrier is an aqueous solution.

35. The pharmaceutical composition of claim 30 wherein the pharmaceutically acceptable carrier comprises a buffer selected from sodium acetate, sodium lactate, sodium chloride, potassium chloride and calcium chloride.

36. The pharmaceutical composition of claim 30 formulated as a tablet, capsule or suppository.

37. The pharmaceutical composition of claim 34 wherein the aqueous solution comprises albumin, lipoprotein or globulin.

38. The pharmaceutical composition of claim 36 further comprising an excipient, vehicle or filler.

39. The pharmaceutical composition of claim 38 comprising 0.1 mg of the peptide.

* * * * *